US007514533B2

(12) United States Patent
Fitzgerald et al.

(10) Patent No.: US 7,514,533 B2
(45) Date of Patent: Apr. 7, 2009

(54) TNF-LIKE SECRETED PROTEIN

(75) Inventors: Stephen Noel Fitzgerald, London (GB); Richard Joseph Fagan, London (GB); Christopher Benjamin Phelps, London (GB); Christine Power, Thoiry (FR); Mark Ibberson, Gimel (CH); Melanie Yorke, Confignon (CH)

(73) Assignee: Ares Trading S.A., Aubonne (CH)

( * ) Notice: Subject to any disclaimer, the term of this patent is extended or adjusted under 35 U.S.C. 154(b) by 63 days.

(21) Appl. No.: 10/557,400

(22) PCT Filed: May 21, 2003

(86) PCT No.: PCT/GB03/02179

§ 371 (c)(1),
(2), (4) Date: Aug. 24, 2006

(87) PCT Pub. No.: WO2004/104040

PCT Pub. Date: Dec. 2, 2004

(65) Prior Publication Data

US 2007/0155958 A1    Jul. 5, 2007

(51) Int. Cl.
  *C07K 17/00*  (2006.01)
  *C12P 21/08*  (2006.01)
  *A61K 38/00*  (2006.01)
(52) U.S. Cl. ............ 530/350; 530/388.22; 514/12
(58) Field of Classification Search .............. None
  See application file for complete search history.

(56) References Cited

U.S. PATENT DOCUMENTS

| 5,252,479 A | 10/1993 | Srivastava |
| 5,608,143 A | 3/1997 | Hershey |
| 5,659,122 A | 8/1997 | Austin |
| 5,693,506 A | 12/1997 | Rodriguez |

FOREIGN PATENT DOCUMENTS

| WO | WO 84/03564 | 9/1984 |
| WO | WO 95/11995 | 5/1995 |
| WO | WO 95/25116 | 9/1995 |
| WO | WO 98/20734 | 5/1998 |
| WO | WO 98/55607 | 12/1998 |
| WO | WO 00/29428 | 5/2000 |
| WO | WO 00/68380 | 11/2000 |
| WO | WO 01/69507 | 9/2001 |
| WO | WO 02/22802 | 3/2002 |
| WO | WO 02/066505 | 8/2002 |

OTHER PUBLICATIONS

Bej, et al., *Crit. Rev. Biochem. Molec. Biol.*, 1991, pp. 301-334, vol. 26.
Berkner, K.L., *Curr. Top. Microbiol. Immunol.*, 1992, pp. 39-66, vol. 158.
Birkenmeyer et al., *J. Virol. Meth.*, 1991, pp. 117-126, vol. 35.
Bodmer et al., *Trends in Biochemical Sciences*, 2002 pp. 19-26, vol. 27, No. 1.
Chee et al., *Science*, 1996, pp. 610-613, vol. 274.
Clackson, T., et al., *Nature*, 1991, pp. 624-628, vol. 352.
Cohen, J.S., *Trends in Pharm. Sci.*, 1989, pp. 435, vol. 10.
Colbere-Garapin, F. et al., *J. Mol. Bio.*, 1981 pp. 1-14, vol. 150.
Cole et al., "Monoclonal Antibodies and Cancer Theraphy", *Alan R. Liss, Inc.*, 1985, pp. 77-96.
Cooney et al., *Science*, 1988, pp. 456, vol. 241.
Cotton, et al., *PNAS USA*, 1985, pp. 4397-4401, vol. 85.
Dervan et al., *Science*, 1991, pp. 1360, vol. 251.
Elbashir, S.M., et al., *Nature*, 2001, pp. 494-498, vol. 411.
Frohman et al., *PNAS USA*, 1988, pp. 8998-9002, vol. 85.
Gorman et al., *Proc. Natl Acade. Sci. USA*, 1991, pp. 34181, vol. 88.
Griffin, A.M., et al., "Computer Analysis of Sequence Data, Part 1, eds."*Humana Press, New Jersey*, 1994.
Hodgson et al., *Bio/Technology*, 1991, pp. 421, vol. 9.
Jones et al., *Nature*, 1986, pp. 522, vol. 321.
Kabat et al., *J. Immunol.*, 1991, pp. 1709-1719, vol. 147.
Kimmel, A.R., *Methods Enzymol.*, 1987, pp. 507-511, vol. 152
Kohler, G., et al. *Nature*, 1975, pp. 495-497, vol. 256.
Kozbor, et al., *Immunology Today*, 1983, pp. 72. vol. 4.
Kroll, D.J., et al., *DNA Cell Biol.*, 1993, pp. 441-453, vol. 12.
Lagerstrom, M., et al., *PCR Methods Applic.*, pp. 111-119, vol. 1. 1991.
Lee et al., *Nucleic Acids Res.*, 1979, pp. 3073, vol. 6.
Liu et al., *Proc. Natl. Acad. Sci. USA*, 1987, pp. 3439, vol. 84.
Lockhart, D.J., *Nat. Biotech.*, 1996, pp. 1675-1680, vol. 14.
Lowy, I., et al., *Cell*, 1980, pp. 817-823, vol. 22.
Maddox, D.E., et al., *J. Exp. Med.*, 1983, pp. 1211-1216, vol. 158.
Marks, J., et al., *Biotechnology*, 1992, pp. 779-783, vol. 10.
McCafferty, J., et al., *Nature*, 1990, pp. 552-554, vol. 348.
Muzyczka, N., *Curr. Top. Microbiol. Immunol.*, 1992, pp. 97-129, vol. 158.
Myers, et al., *Science*, 1985, pp. 1242, vol. 230.
Nielsen, P.E., et al., *Anticancer Drug Des.*, 1993, pp. 53-63, vol. 8.
Okano, J., *Neurochem.*, 1991, pp. 560, vol. 56.
Orita, et al., *Genomics*, 1989, pp. 874-879, vol. 5.
Parker, J.D., et al., *Nucleic Acids Res.*, 1991, pp. 3055-3060, vol. 19.
Porath, J., et al., *Prot. Exp. Purif.*, 1992, pp. 263-281, vol. 3.
Queen, et al., *PNAS USA*, 1989, pp. 10029, vol. 86.
Saiki et al., *Nature*, 1986, pp. 163-166, vol. 324.
Sakkar, G., *PCR Methods Applic.*, 1993, pp. 318-322, vol. 2.
Schena, M., et al., *PNAS* 1996, pp. 10614-10619, vol. 93.
Tkachuk et al., 1990, pp. 559-562, vol. 250.
Trask et al., *Trends, Genet.*, 1991, pp. 149-154, vol. 7.

(Continued)

*Primary Examiner*—Robert Landsman
*Assistant Examiner*—Ian Dang
(74) *Attorney, Agent, or Firm*—Saliwanchik, Lloyd & Saliwanchik

(57) ABSTRACT

This invention relates to novel protein INSP058, herein identified as TNF-like secreted protein, and to the use of this protein and the nucleic acid sequence from the encoding gene in the diagnosis, prevention, and treatment of disease.

6 Claims, 18 Drawing Sheets

OTHER PUBLICATIONS

Triglia, T., et al., *Nucleic Acids Res.*, 1988, pp. 8186, vol. 16.
Usman, N., et al., *Curr. Opin. Struct. Biol.* 1996, pp. 527-533, vol. 6, No. 4.
Van Brunt, J., *Bio/Technology*, 1990, pp. 291-294, vol. 8.
Verhoeyen et al., *Science*, 1988, pp. 1534, vol. 239.
Wahl, G.M., et al., *S.L. Berger Methods Enzymol.*, 1987, pp. 399-407, vol. 152.
Wigler, M., et al., *Cell*. 1977, pp. 223-232, vol. 11.
Wigler, M., et al., *PNAS*, 1980, pp. 3567-3570, vol. 77.
Zenk, *Phytochemistry*, 1991, pp. 3861-3863, vol. 30.
Berner, B. et al. "Rapid improvement of SLE-specific cutaneous lesions by C1q immunoadsorption" *Ann. Rheum Dis,* 2001, pp. 898-899, vol. 60, No. 9.
Lu, J. et al. "The Classical and Regulatory Functions of C1q in Immunity and Autoimmunity" *Cellular & Molecular Immunology,* Feb. 2008, pp. 9-21, vol. 5, No. 1.
Fonseca, M.I. et al. "Absence of C1q Leads to Less Neuropathy in Transgenic Mouse Models of Alzheimers's Disease" *The Journal of Neuroscience,* Jul. 21, 2004, pp. 6465-6457, vol. 24, No. 29.

FIG. 1
Top ten NCBI non-redundant database BLAST hits against INSP058 (full protein sequence)

```
Query= INSP058
        (333 letters)

Database: ncbi-nr
          920,511 sequences; 288,591,484 total letters

Searching..............................................done

Score     E
Sequences producing significant alignments:                (bits)
Value dbj|BAB84561.1| (AB067770) otolin-1 [Oncorhynchus keta]     285   5e-76
ref|XP_067228.1| (XM_067228) similar to INNER EAR-SPECIFIC COLLA... 250   1e-65
sp|P98085|COLE_LEPMA INNER EAR-SPECIFIC COLLAGEN PRECURSOR (SACC... 250   2e-65
ref|XP_060619.1| (XM_060619) similar to COLLAGEN ALPHA 2(VIII) C... 242   3e-63
dbj|BAB84955.1| (AK074129) FLJ00201 protein [Homo sapiens]  242   3e-63
sp|P25067|CA28_HUMAN Collagen alpha 2(VIII) chain (Endothelial c... 236   3e-61
sp|P08125|CA1A_CHICK COLLAGEN ALPHA 1(X) CHAIN PRECURSOR    234   9e-61
sp|P23206|CA1A_BOVIN COLLAGEN ALPHA 1(X) CHAIN PRECURSOR >gi|108... 233   2e-60
pir||S23297 collagen alpha 1(X) chain precursor - chicken   232   3e-60
emb|CAA42933.1| (X60382) collagen subunit  (alpha-1 (X)) 3 [Homo... 231   8e-60
```

FIG. 2

```
>dbj|BAB84561.1| (AB067770) otolin-1 [Oncorhynchus keta]
          Length = 508

Score =  285 bits (729), Expect = 5e-76
 Identities = 160/342 (46%), Positives = 207/342 (59%), Gaps = 35/342 (10%)

Query: 25  QGHPGIPGNPGHNGLPGRDGRDGAKGDKGDAGEPGRPGSPG---KDGTSGEKGERGADGK 81
           +G  G+ G PG +G+PG   G +G KGDKGD G+ G PG+PG    K+G  G+ G +G G+
Sbjct: 167 KGDVGLMGPPGLDGMPGATGLEGDKGDKGDQGDTGMPGAPGILGKEGPKGDLGPKGEKGE 226

Query: 82  VEAKGIKGDQGSRGSPGKHG---------------PKGLAGPMGEKGLRGETG--PQGQK 124
           G+KGD G RG PG +G              P GL GPMG+ G +GE G  P G+K
Sbjct: 227 TGLPGLKGDLGERGKPGWNGTQGEKGDLGKIGPAGPSGLTGPMGQNGQKGEMGECPTGEK 286

Query: 125 GNKGDVGPTGPEGPRGNIGPLG---PTGLPGPMG---PIGKPGPKGEAGPTGP---QGEP 175
           G KG+ G GP GPRG +G G    GLPGP+G   +G PG KGEAG GP   +G P
Sbjct: 287 GEKGEAGLPGPPGPRGLVGTPGVNGTNGLPGPVGLRGQLGSPGGKGEAGGRGPPGLRGMP 346

Query: 176 GVRGIRGWKGDRG---EKGKIGETLVLPKSAFTVGLTVLSKFPSSDMPIKFDKILYNEFN 232
           G +G +G KG RG    KG GET   +SAF+VGL    FP  +P+KFDKILYNE
Sbjct: 347 GPKGEKGPKGPRGVRGPKGPQGETAEQIRSAFSVGLFPSKSFPPPGLPVKFDKILYNEEE 406

Query: 233 HYDTAAGKFTCHIAGVYYFTYHITVFSRNVQVSLVKNGVKILHTKDA-YMSSEDQASGGI 291
           H+D  KF C  GVY F+YHITV +R ++ +LV NGVK L T+D+ Y    DQAS
Sbjct: 407 HWDPMLSKFNCTHPGVYVFSYHITVRNRPLRAALVINGVKKLRTRDSLYGQDIDQASNLA 466

Query: 292 VLQLKLGDEVWLQVTGGERFNGLFADEDDDTTFTGFLLFSSP 333
           +L+L GD+VWL+     +NG+++ +DD+TFTGFLL++ P
Sbjct: 467 LLRLASGDQVWLETL--RDWNGVYSSSEDDSTFTGFLLYADP 506
```

FIG. 3

Genome Threader results
Genome Threader results - Energy Scores

| Num | PDB Code | Norm Align Score | Raw Align Score | %IDs | %Struct Aligned | %Query Seq Aligned | Pairwise Energy | Solvation Energy | Neural Net Score | %Confidence | From Pos for Query | To Pos for Query | From Pos for Target | To Pos for Target | Alignment Length | Local=0 Global=1 |
|---|---|---|---|---|---|---|---|---|---|---|---|---|---|---|---|---|
| 1 | 1c28AA00 biopendium (align) | 357.44 | 386 | 47.7 | 97.6 | 39.6 | -106.43 | -3.13 | 0.987 | 100 | 199 | 330 | 1 | 122 | 132 | 0 |
| 2 | 1c28CC00 biopendium (align) | 276.32 | 304 | 43.2 | 98.0 | 39.6 | -1.07 | -1.89 | 0.987 | 100 | 199 | 330 | 1 | 100 | 132 | 0 |
| 3 | 1c28BB00 biopendium (align) | 270.95 | 299 | 44.2 | 95.5 | 38.7 | -0.98 | -2.98 | 0.987 | 100 | 201 | 329 | 3 | 108 | 129 | 0 |
| 4 | 1d8kAA00 biopendium (align) | 35.33 | 72 | 16.1 | 17.5 | 45.6 | 19.89 | 1.74 | 0.944 | 73 | 158 | 309 | 607 | 751 | 155 | 0 |
| 5 | 1bziBB00 biopendium (align) | 31.15 | 59 | 14.9 | 86.8 | 29.7 | 0.00 | -1.29 | 0.929 | 66 | 228 | 326 | 11 | 102 | 101 | 0 |
| 6 | 1d2qAA00 biopendium (align) | 30.14 | 59 | 23.4 | 65.7 | 27.0 | -12.41 | 1.70 | 0.915 | 60 | 239 | 328 | 44 | 131 | 94 | 0 |
| 7 | 2staBE00 biopendium (align) | 27.97 | 59 | 29.7 | 16.7 | 11.1 | -0.30 | -0.60 | 0.904 | 57 | 17 | 53 | 141 | 177 | 37 | 0 |
| 8 | 1qc1AA00 biopendium (align) | 27.12 | 57 | 35.2 | 29.4 | 15.3 | 2.03 | 0.07 | 0.894 | 53 | 47 | 97 | 117 | 166 | 54 | 0 |
| 9 | 1sat-100 biopendium (align) | 25.75 | 60 | 36.7 | 6.4 | 9.0 | 15.46 | 1.50 | 0.871 | 47 | 25 | 54 | 332 | 361 | 30 | 0 |
| 10 | 1ez1AA00 biopendium (align) | 25.55 | 59 | 14.7 | 23.9 | 28.5 | -10.24 | 3.49 | 0.858 | 44 | 191 | 285 | 20 | 112 | 95 | 0 |
| 11 | 1cq2AA00 biopendium (align) | 24.55 | 58 | 18.5 | 16.2 | 19.2 | 26.71 | 1.52 | 0.854 | 43 | 35 | 98 | 150 | 212 | 65 | 0 |
| 12 | 1pvtDD00 biopendium (align) | 23.44 | 55 | 18.5 | 19.5 | 16.2 | 15.28 | 2.81 | 0.827 | 38 | 12 | 65 | 185 | 233 | 54 | 0 |
| 13 | 1tnrAA00 biopendium (align) | 22.83 | 52 | 16.7 | 50.0 | 25.2 | -39.72 | -1.09 | 0.844 | 41 | 245 | 328 | 71 | 142 | 84 | 0 |
| 14 | 1rypBE00 biopendium (align) | 22.60 | 54 | 17.1 | 28.9 | 16.2 | -6.75 | -2.60 | 0.849 | 42 | 254 | 307 | 3 | 72 | 70 | 0 |
| 15 | 1rypBB00 biopendium (align) | 22.46 | 54 | 18.6 | 28.0 | 16.2 | -2.26 | -2.47 | 0.846 | 41 | 254 | 307 | 8 | 77 | 70 | 0 |
| 16 | 1chmAA00 biopendium (align) | 22.42 | 56 | 22.7 | 9.5 | 13.2 | 1.87 | 2.27 | 0.812 | 35 | 174 | 217 | 357 | 394 | 44 | 0 |
| 17 | 1cruBB00 biopendium (align) | 21.90 | 56 | 17.4 | 37.6 | 45.3 | 100.88 | 2.13 | 0.799 | 33 | 29 | 179 | 137 | 306 | 178 | 0 |
| 18 | 1etu-100 biopendium (align) | 20.94 | 51 | 19.5 | 43.5 | 21.0 | 8.48 | -0.50 | 0.804 | 34 | 235 | 304 | 15 | 91 | 77 | 0 |
| 19 | 1alv-100 biopendium (align) | 20.77 | 50 | 20.4 | 66.4 | 25.8 | -99.12 | -3.83 | 0.826 | 38 | 243 | 328 | 48 | 144 | 103 | 0 |
| 20 | 3bc2-100 biopendium (align) | 18.11 | 49 | 12.2 | 45.1 | 33.6 | -74.05 | -3.31 | 0.762 | 28 | 220 | 331 | 64 | 160 | 115 | 0 |

<<Previous 1 2 Next>>

The top three PDB codes in Figure 3 refer to the following protein structure:

Number 1,2 and 3: 1c28 chains A, C and B: The crystal structure of a complement-1q family protein suggests an evolutionary link to tumor necrosis factor.

FIG. 4 Genome Threader structural alignment between INSP058 and the top PDB structure in Figure 3 (lc28)

```
Alignment Type:       Local
Sequence A Range:     1 -> 125
Sequence B Range:     1 -> 333
Gap Open Penalty:     -11
Gap Extend Penalty:   -1
Scoring Matrix:       /usr/local/BLOSUM62
Profile A:            ./gtws_files/profiles/1c28AA00.pro
Sequence B:           /tmp/gtw_14201.fa
DB Alignment:         -
GT Alignment:         -
View Alignment:       Yes
Reverse GT Alignment: No
SCORES:  Score Length Num_ID No. +ve  OvrlP  %ID   %+ve  From  To   From  To
         386    132    63     96     135    47.7  72.7  1     125  122   199  330
SCORE2:  Length1 Length2 Normalised-Score
         125     333     357.443100

1c28AA00   ------------------------------------------------------------

INSP058    mriwwlllalelctgninsqdtcrqghpgipgnpghnglpgrdgrdgakgdkgdagepgrpgspgkdgts
           10|       20|       30|       40|       50|       60|       70|

1c28AA00   ------------------------------------------------------------

INSP058    gekgergadgkveakgdqgsrgspgkhgpkglagpmgekglrgetgpqgqkgnkgdvgptgpegprg
           80|       90|       100|      110|      120|      130|      140|

1c28AA00   ----------------------------------------MYRSAFSVGLE-
                                                   :::: : :::
INSP058    nigplgptglpgpmgpigkpgpkgeagptgpqgepgvrgirgwkgdrgekgigetlvLPKSAFTVGLTV
           150|      160|      170|      180|      190|      200|      210|

1c28AA00   -TRVTVPNVPIRFTKIFYNQQNHYDGSTGKFYCNIPGLYYFSYHITVYMKDVRVSLFKKDKAVLFTYDQY
            :::::::::: :: :: ::::::::::::::::::::::::::::::::::::::::::::::::::
INSP058    LSKFPSSDMPIKFDKILYNEFNHYDTAAGKFTCHIAGVYYFTYHITVFSRNVQVSLVKNGVKILHTKDAY
           220|      230|      240|      250|      260|      270|      280|

1c28AA00   QENVDQASGSVLLHLEVGDQVWLQVYYA------DNVNDSTFTGFLLYhdt
           ::::::::::::::::::::::::::::      :::::::::::::
INSP058    MSSEDQASGGIVLQLKLGDEVWLQVTGGERFNGLFADEDDDTTFTGFLLFssp
           290|      300|      310|      320|      330|
```

FIG. 6

```
  1 atgaggatct ggtggcttct gcttgccatt gaaatctgca cagggaacat aaactcacag
    m  r  i   w  w  l  l   l  a  i    e  i  c    t  g  n    i  n  s  q
              INSP058-CP1
 61 gacacctgca ggcaagggca ccctggaatc cctgggaacc ccggtcacaa tggtctgcct
    d  t  c    r  q  g    h  p  g  i   p  g  n    p  g  h    n  g  l  p
121 ggaagagatg gacgagacgg agcgaagggt gacaaaggcg atgcaggaga accaggacgt
    g  r  d    g  r  d    g  a  k  g   d  k  g    d  a  g    e  p  g  r
181 cctggcagcc cggggaagga tgggacgagt ggagagaagg gagaacgagg agcagatgga
    p  g  s    p  g  k    d  g  t  s   g  e  k    g  e  r    g  a  d  g
241 aaagttgaag caaaaggcat caaaggtgat caaggctcaa gaggatcccc aggaaaacat
    k  v  e    a  k  g    i  k  g  d   q  g  s    r  g  s    p  g  k  h
301 ggccccaagg ggcttgcagg gcccatggga gagaagggcc tccgaggaga gactgggcct
    g  p  k    g  l  a    g  p  m  g   e  k  g    l  r  g    e  t  g  p
361 caggggcaga aggggaataa gggtgacgtg gtcccactg gtcctgaggg gccaaggggc
    q  g  q    k  g  n    k  g  d  v   g  p  t    g  p  e    g  p  r  g
421 aacattgggc ctttgggccc aactggttta ccgggcccca tgggccctat tggaaagcct
    n  i  g    p  l  g    p  t  g  l   p  g  p    m  g  p    i  g  k  p
481 ggtcccaaag gagaagctgg acccacgggg ccccagggtg agccaggagt ccggggaata
    g  p  k    g  e  a    g  p  t  g   p  q  g    e  p  g    v  r  g  i
541 agaggctgga aaggagatcg aggagagaaa gggaaaatcg gtgagactct agtcttgcca
    r  g  w    k  g  d    r  g  e  k   g  k  i    g  e  t    l  v  l  p
601 aaaagtgctt tcactgtggg gctcacggtg ctgagcaagt ttccttcttc agatatgccc
    k  s  a    f  t  v    g  l  t  v   l  s  k    f  p  s    s  d  m  p
661 attaaatttg ataagatcct gtataacgaa ttcaaccatt atgatacagc agcggggaaa
    i  k  f    d  k  i    l  y  n  e   f  n  h    y  d  t    a  a  g  k
721 ttcacgtgcc acattgctgg ggtctattac ttcacctacc acatcactgt tttctccaga
    f  t  c    h  i  a    g  v  y  y   f  t  y    h  i  t    v  f  s  r
781 aatgttcagg tgtctttggt caaaaatgga gtaaaaatac tgcacaccaa agatgcttac
    n  v  q    v  s  l    v  k  n  g   v  k  i    l  h  t    k  d  a  y
841 atgagctctg aggaccaggc ctctggcggc attgtcctgc agctgaagct cggggatgag
    m  s  s    e  d  q    a  s  g  g   i  v  l    q  l  k    l  g  d  e
901 gtgtggctgc aggtgacagg aggagagagg ttcaatggct gtttgctga tgaggacgat
    v  w  l    q  v  t    g  g  e  r   f  n  g    l  f  a    d  e  d  d
961 gacacaactt tcacagggtt ccttctgttc agcagcccgt ga
    d  t  t    f  t  g   f  l  l  f   s  s  p    -
                         INSP058-CP2
```

Position and sense of PCR primers

FIG. 7

```
  1  ctggtggctt ctgcttgcca ttgaaatctg cacagggaac ataaactcac aggacacctg
        w   w  l    l   l   a   i   e   i   c   t   g   n   i   n   s   q   d   t 61  caggcaaggg caccctggaa tccctgggaa ccccggtcac aatggtctgc ctggaagaga
        c   r   q   g   h   p   g   i   p   g   n   p   g   h   n   l   p   g   r 121  tggacgagac ggagcgaagg gtgacaaagg cgatgcagga gaaccaggat gtcctggcag
        d   g   r   d   g   a   k   g   d   k   g   d   a   g   e   p   g   c   p   g 181  cccggggaag gatgggacga gtggagagaa gggagaacga ggagcagatg gaaaagttga
        s   p   g   k   d   g   t   s   g   e   k   g   e   r   g   a   d   g   k   v 241  agcaaaaggc atcaaaggaa tgttcaggtg tctttggtca aaaacggagt aaaaatactg
        e   a   k   g   i   k   g   m   f   r   c   l   w   s   k   t   e   -   k   y 301  cacaccagag atgcttacgt gagctctgag gaccaggcct ctggcagcat tgtcctgcag
        c   t   p   e   m   l   t   -   a   l   r   t   r   p   l   a   a   l   s   c 361  ctgaagctcg gggatgagat gtggctgcag gtgacaggag gagagaggtt caatggcttg
        s   -   s   s   g   m   r   c   g   c   r   -   q   e   e   r   g   s   m   a 421  tttgctgatg aggacgatga cacaactttc acagggttcc ttctgttcag cagccc
        c   l   l   m   r   t   m   t   q   l   s   q   g   s   f   c   s   a   a
```

FIG. 8

```
Molecule:    INSP058sv, 4426 bps DNA Circular
File Name:   12917[1].cm5

Molecule Features:

Type      Start   End    Name       Description
REGION        1   336    LacZa'
MARKER      239          SP6 prom
GENE        337   812    PCR product insert 6A3/6A4 PCR product
                                    missing first 8bp of cds (ATGAGGAT)
REGION      813  1064    'LacZa
MARKER      882       C  T7 prom
REGION     1066  1480    f1 ori
GENE       1814  2608    KanR
GENE       2626  3486    AmpR
REGION     3631  4304    pUC ori
```

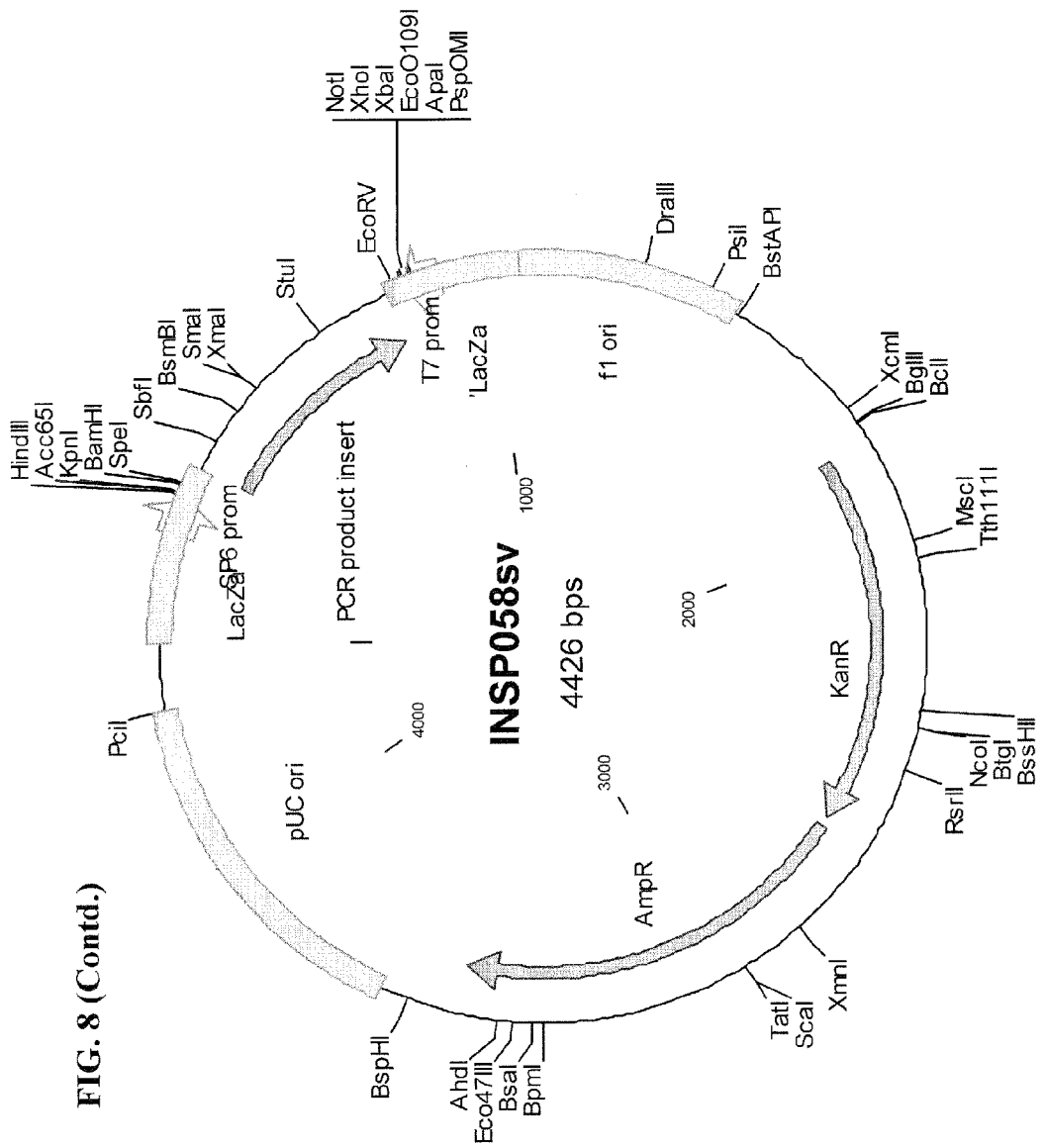
FIG. 8 (Contd.)

```
INSP058      ---------------------------------------------ATGAGGATCTGGTGG
INSP058SV    -------------------------------------------------CTGGTGG
                                                              ******

INSP058      CTTCTGCTTGCCATTGAAATCTGCACAGGGAACATAAACTCACAGGACACCTGCAGGCAA
INSP058SV    CTTCTGCTTGCCATTGAAATCTGCACAGGGAACATAAACTCACAGGACACCTGCAGGCAA
             ************************************************************

INSP058      GGGCACCCTGGAATCCCTGGGAACCCCGGTCACAATGGTCTGCCTGGAAGAGATGGACGA
INSP058SV    GGGCACCCTGGAATCCCTGGGAACCCCGGTCACAATGGTCTGCCTGGAAGAGATGGACGA
             ************************************************************

INSP058      GACGGAGCGAAGGGTGACAAAGGCGATGCAGGAGAACCAGGACGTCCTGGCAGCCCGGGG
INSP058SV    GACGGAGCGAAGGGTGACAAAGGCGATGCAGGAGAACCAGGATGTCCTGGCAGCCCGGGG
             *****************************************  ****************

INSP058      AAGGATGGGACGAGTGGAGAGAAGGGAGAACGAGGAGCAGATGGAAAAGTTGAAGCAAAA
INSP058SV    AAGGATGGGACGAGTGGAGAGAAGGGAGAACGAGGAGCAGATGGAAAAGTTGAAGCAAAA
             ************************************************************

INSP058      GGCATCAAAGGTGATCAAGGCTCAAGAGGATCCCCAGGAAAACATGGCCCCAAGGGGCTT
INSP058SV    GGCATCAAAGG-------------------------------------------------
             ***********

INSP058      GCAGGGCCCATGGGAGAGAAGGGCCTCCGAGGAGAGACTGGGCCTCAGGGGCAGAAGGGG
INSP058SV    ------------------------------------------------------------

INSP058      AATAAGGGTGACGTGGGTCCCACTGGTCCTGAGGGGCCAAGGGGCAACATTGGGCCTTTG
INSP058SV    ------------------------------------------------------------

INSP058      GGCCCAACTGGTTTACCGGGCCCCATGGGCCCTATTGGAAAGCCTGGTCCCAAAGGAGAA
INSP058SV    ------------------------------------------------------------

INSP058      GCTGGACCCACGGGGCCCCAGGGTGAGCCAGGAGTCCGGGGAATAAGAGGCTGGAAAGGA
INSP058SV    ------------------------------------------------------------

INSP058      GATCGAGGAGAGAAAGGGAAAATCGGTGAGACTCTAGTCTTGCCAAAAAGTGCTTTCACT
INSP058SV    ------------------------------------------------------------

INSP058      GTGGGGCTCACGGTGCTGAGCAAGTTTCCTTCTTCAGATATGCCCATTAAATTTGATAAG
INSP058SV    ------------------------------------------------------------

INSP058      ATCCTGTATAACGAATTCAACCATTATGATACAGCAGCGGGGAAATTCACGTGCCACATT
INSP058SV    ------------------------------------------------------------

INSP058      GCTGGGGTCTATTACTTCACCTACCACATCACTGTTTTCTCCAGAAATGTTCAGGTGTCT
INSP058SV    ----------------------------------------------AATGTTCAGGTGTCT
                                                           ***************

INSP058      TTGGTCAAAAATGGAGTAAAAATACTGCACACCAAAGATGCTTACATGAGCTCTGAGGAC
INSP058SV    TTGGTCAAAAACGGAGTAA
             ******************

INSP058      CAGGCCTCTGGCGGCATTGTCCTGCAGCTGAAGCTCGGGGATGAGGTGTGGCTGCAGGTG

INSP058      ACAGGAGGAGAGAGGTTCAATGGCTTGTTTGCTGATGAGGACGATGACACAACTTTCACA

INSP058      GGGTTCCTTCTGTTCAGCAGCCCGTGA
```

FIG. 9

(Stop codons highlighted in reverse)

FIG. 10

```
INSP058      MRIWWLLLAIEICTGNINSQDTCRQGHPGIPGNPGHNGLPGRDGRDGAKGDKGDAGEPGR
INSP058SV    MRIWWLLLAIEICTGNINSQDTCRQGHPGIPGNPGHNGLPGRDGRDGAKGDKGDAGEPGC
             ************************************************************

INSP058      PGSPGKDGTSGEKGERGADGKVEAKGIKGDQGSRGSPGKHGPKGLAGPMGEKGLRGETGP
INSP058SV    PGSPGKDGTSGEKGERGADGKVEAKGIKGMFRCLWSKTE---------------------
             *****************************

INSP058      QGQKGNKGDVGPTGPEGPRGNIGPLGPTGLPGPMGPIGKPGPKGEAGPTGPQGEPGVRGI
INSP058SV    ------------------------------------------------------------

INSP058      RGWKGDRGEKGKIGETLVLPKSAFTVGLTVLSKFPSSDMPIKFDKILYNEFNHYDTAAGK
INSP058SV    ------------------------------------------------------------

INSP058      FTCHIAGVYYFTYHITVFSRNVQVSLVKNGVKILHTKDAYMSSEDQASGGIVLQLKLGDE
INSP058SV    ------------------------------------------------------------

INSP058      VWLQVTGGERFNGLFADEDDDTTFTGFLLFSSP
INSP058SV    --------------------------------
```

FIG. 11

Molecule:     pEAK12 d,  8760 bps DNA Circular
File Name:    pEAK12DEST.cm5

Description:  Mammalian cell expression vector (plasmid ID 11345)

Molecule Features:

| Type | Start | End | Name | Description |
|---|---|---|---|---|
| REGION | 2 | 595 |  | pmb-ori |
| GENE | 596 | 1519 | Amp |  |
| REGION | 1690 | 2795 | EF-1alpha |  |
| REGION | 2703 | 2722 |  | position of pEAK12F primer |
| REGION | 2796 | 2845 |  | MCS |
| MARKER | 2855 |  | attR1 |  |
| GENE | 3256 | 3915 | CmR |  |
| GENE | 4257 | 4562 | ccdB |  |
| MARKER | 4603 |  | C attR2 |  |
| REGION | 4733 | 4733 |  | MCS |
| REGION | 4734 | 5162 |  | poly A/splice |
| REGION | 4819 | 4848 | C | position of pEAK12R primer |
| GENE | 5781 | 5163 | C PUR | PUROMYCIN |
| REGION | 6005 | 5782 | C tK | tK promoter |
| REGION | 6500 | 6006 | C Ori P |  |
| GENE | 8552 | 6500 | C EBNA-1 |  |
| REGION | 8553 | 8752 | sv40 |  |

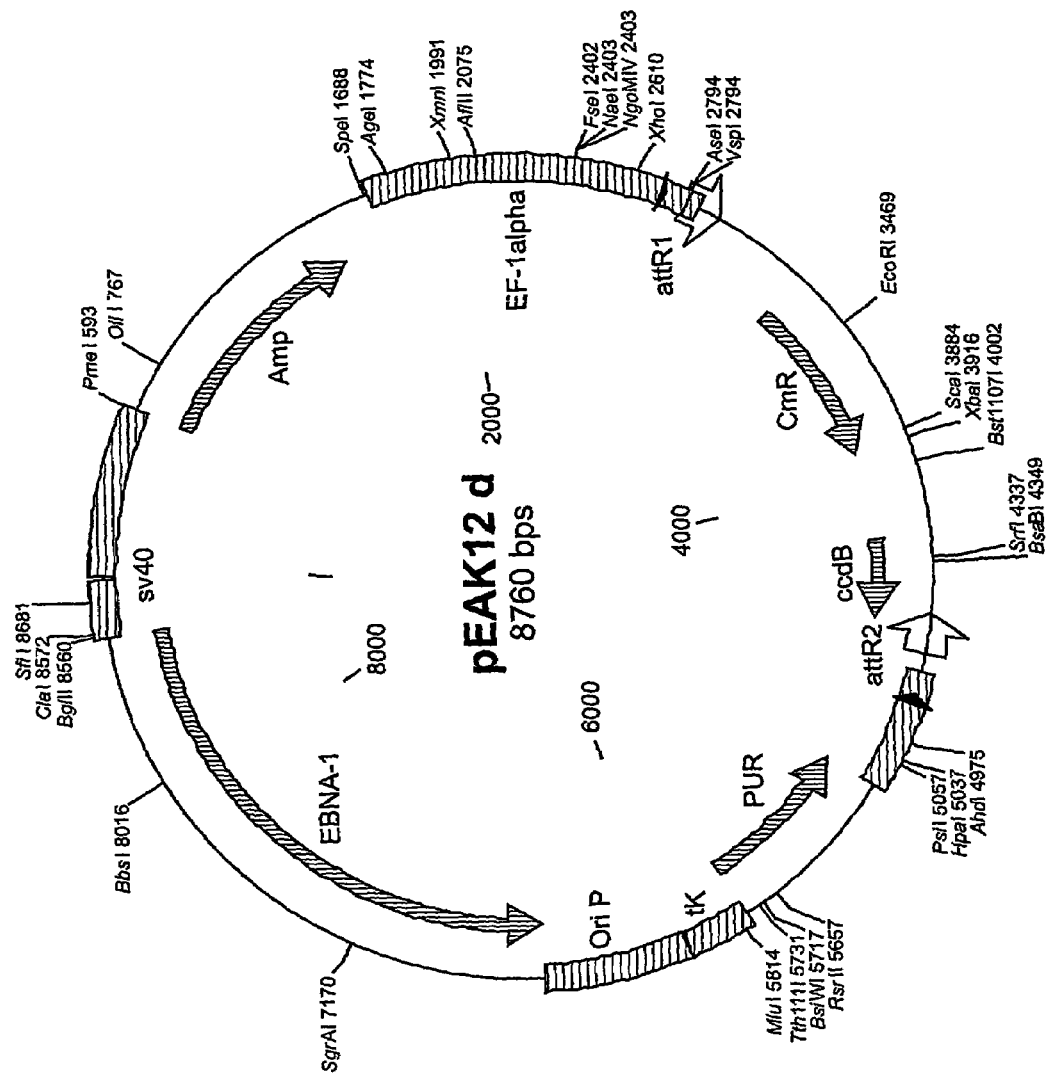
FIG. 11(Contd.)

FIG. 12

Molecule:      pDONR201, 4470 bps DNA Circular
File Name:     pDONR201.cm5

Description:   Gateway entry vector (Invitrogen)- plasmid ID# 13309

Molecule Features:

| Type   | Start | End  | Name   |
|--------|-------|------|--------|
| REGION | 332   | 563  | attP1  |
| GENE   | 959   | 1264 | ccdB   |
| REGION | 2513  | 2744 | attP2  |
| GENE   | 2868  | 3677 | KanR   |
| REGION | 3794  | 4467 | pUC ori |

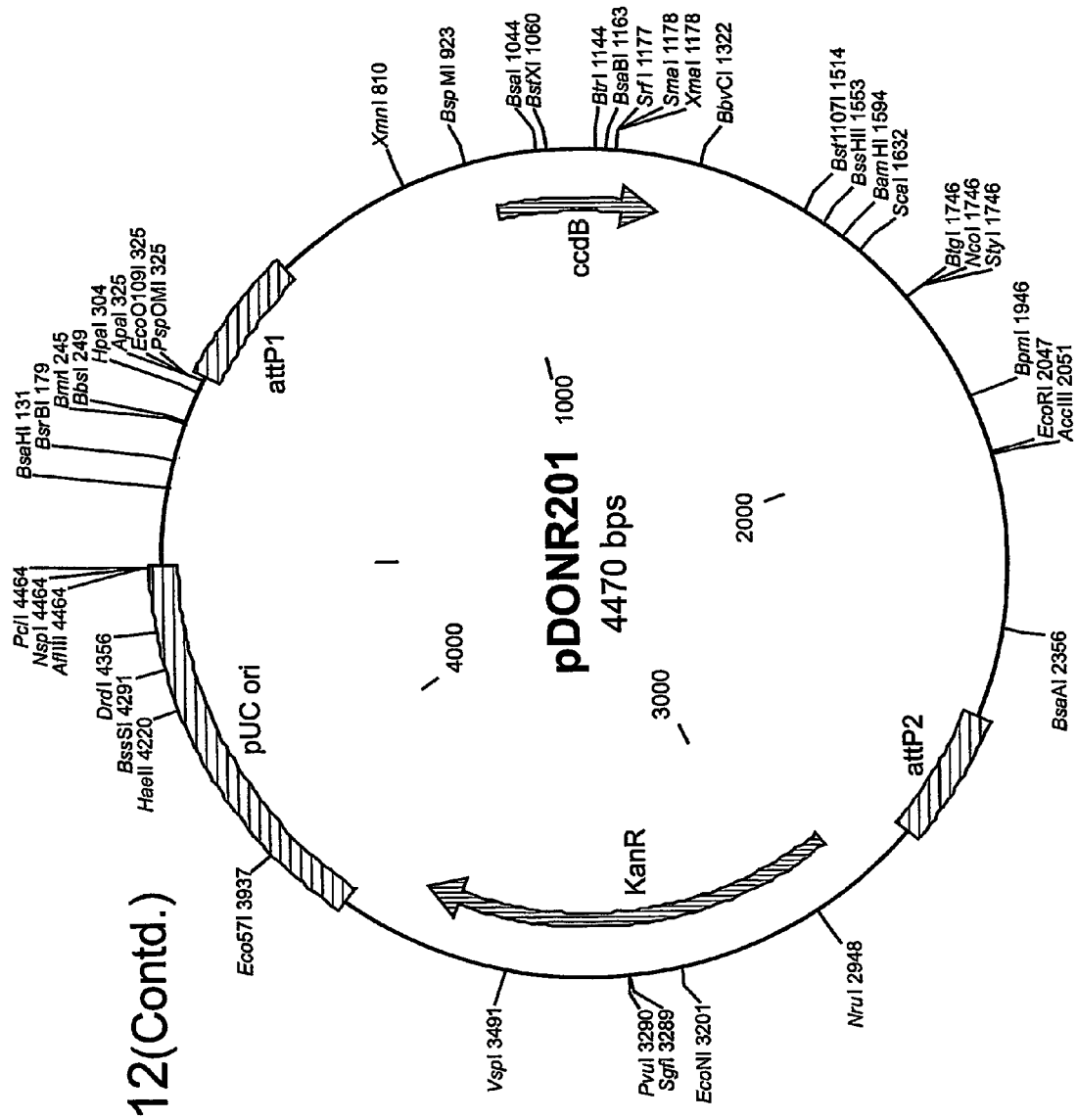
FIG. 12(Contd.)

FIG. 13

Molecule:      INSP058SV-6HIS,  7267 bps DNA Circular
File Name:     pEAK12d-INSP058SV-6HIS.cm5

Molecule Features:

| Type   | Start | End    | Name    | Description              |
|--------|-------|--------|---------|--------------------------|
| REGION | 2     | 595    |         | pmb-ori                  |
| GENE   | 596   | 1519   | AmpR    | ampicillin resistance gene |
| REGION | 1690  | 2795   | EF-1alpha | promoter               |
| MARKER | 2703  |        |         | pEAK12 F primer          |
| REGION | 2796  | 2845   |         | MCS''                    |
| REGION | 2855  | 2874   |         | attB1                    |
| GENE   | 2888  | 3205   |         | INSP058SV cds            |
| REGION | 3213  | 3234   |         | attB2                    |
| REGION | 3240  | 3240   |         | 'MCS                     |
| REGION | 3241  | 3669   |         | poly A/splice            |
| MARKER | 3355  | C      |         | pEAK12R primer           |
| GENE   | 4288  | 3670 C |         | Puromycin resistance gene |
| REGION | 4512  | 4289 C | tK      | tK promoter              |
| REGION | 5007  | 4513 C | Ori P   |                          |
| GENE   | 7059  | 5007 C | EBNA-1  |                          |
| REGION | 7060  | 7259   | sv40    |                          |

FIG. 13(Contd.)
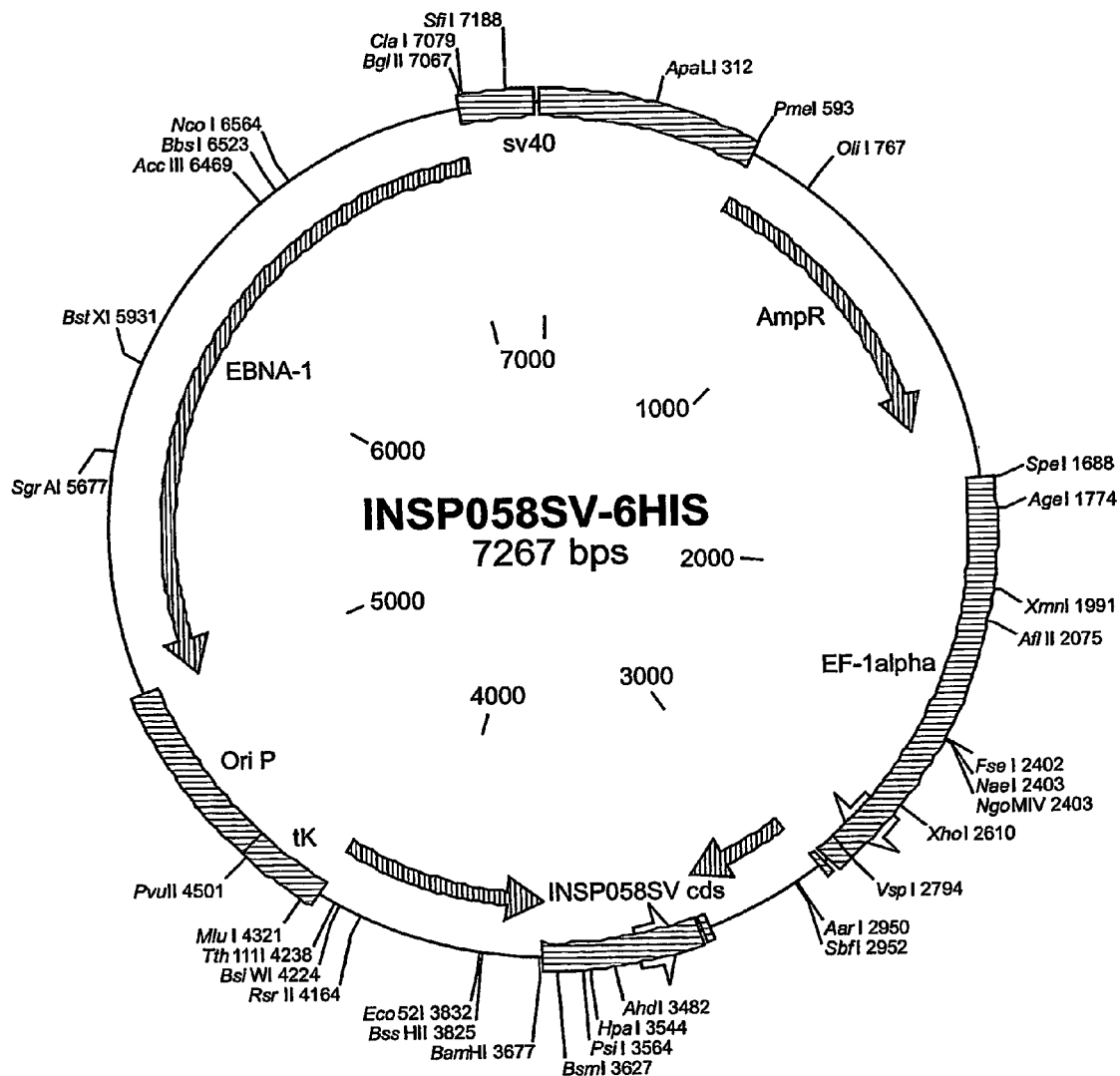

TNF-LIKE SECRETED PROTEIN

CROSS-REFERENCE TO RELATED APPLICATION

This application is the National Stage of International Application Number PCT/GB2003/002179, filed May 21, 2003, which is hereby incorporated by reference herein in its entirety, including any figures, tables, nucleic acid sequences, amino acid sequences, or drawings.

The Sequence Listing for this application is on duplicate compact discs labeled "Copy 1" and "Copy 2." Copy 1 and Copy 2 each contain only one file named "Aug06.txt" which was created on Jul. 12, 2006, and is 18 KB. The entire contents of each of the computer discs are incorporated herein by reference in their entireties.

This invention relates to a novel protein, termed INSP058, herein identified as a TNF-like secreted protein, and to the use of this protein and the nucleic acid sequence from the encoding gene in the diagnosis, prevention and treatment of disease.

All publications, patents and patent applications cited herein are incorporated in full by reference.

BACKGROUND

The process of drug discovery is presently undergoing a fundamental revolution as the era of functional genomics comes of age. The term "functional genomics" applies to an approach utilising bioinformatics tools to ascribe function to protein sequences of interest. Such tools are becoming increasingly necessary as the speed of generation of sequence data is rapidly outpacing the ability of research laboratories to assign functions to these protein sequences.

As bioinformatics tools increase in potency and in accuracy, these tools are rapidly replacing the conventional techniques of biochemical characterisation. Indeed, the advanced bioinformatics tools used in identifying the present invention are now capable of outputting results in which a high degree of confidence can be placed.

Various institutions and commercial organisations are examining sequence data as they become available and significant discoveries are being made on an on-going basis. Incyte Genomics, Inc., for example, have a published patent application (WO 00/68380) relating to sequences associated with human extracellular matrix and adhesion-associated proteins (EXMAD) and polynucleotides which identify and encode EXMAD. However, there remains a continuing need to identify and characterise further genes and the polypeptides that they encode, as targets for research and for drug discovery.

Secreted Proteins

The ability of cells to make and secrete extracellular proteins is central to many biological processes. Enzymes, growth factors, extracellular matrix proteins and signalling molecules are all secreted by cells. This is through fusion of a secretory vesicle with the plasma membrane. In most cases, but not all, proteins are directed to the endoplasmic reticulum and into secretory vesicles by a signal peptide. Signal peptides are cis-acting sequences that affect the transport of polypeptide chains from the cytoplasm to a membrane bound compartment such as a secretory vesicle. Polypeptides that are targeted to the secretory vesicles are either secreted into the extracellular matrix or are retained in the plasma membrane. The polypeptides that are retained in the plasma membrane will have one or more transmembrane domains. Examples of secreted proteins that play a central role in the functioning of a cell are cytokines, hormones, extracellular matrix proteins (adhesion molecules), proteases, TNF-like proteins and growth and differentiation factors.

Alteration of the activity of secreted proteins thus provides a means to alter disease phenotype and as such, identification of novel secreted proteins, particularly TNF-like secreted proteins, is highly relevant as they may play a role in certain diseases and thus be useful in the development of novel therapies.

THE INVENTION

The invention is based on the discovery that the INSP058 protein is a TNF-like secreted protein. In one embodiment of the first aspect of the invention, there is provided a polypeptide which:

(i) comprises the amino acid sequence as recited in SEQ ID NO:8 and/or SEQ ID NO:12;
(ii) is a fragment thereof which is a TNF-like secreted protein, or having an antigenic determinant in common with the polypeptides of (i); or
(iii) is a functional equivalent of (i) or (ii).

According to a second embodiment of this first aspect of the invention, there is provided a polypeptide which:

(i) consists of the amino acid sequence as recited in SEQ ID NO:8 and/or SEQ ID NO:12,
(ii) is a fragment thereof having the function of a TNF-like secreted protein, or having an antigenic determinant in common with the polypeptide of (i); or
(iii) is a functional equivalent of (i) or (ii).

Preferably, the fragment or functional equivalent of the first or second embodiments consists of the amino acid recited in SEQ ID NO:9 or SEQ ID NO:16.

The polypeptide having the sequence recited in SEQ ID NO:8 is referred to hereafter as "the INSP058 polypeptide". This protein is annotated herein as a TNF-like secreted protein. The closest link identified for this protein to proteins of known function is to complement 1q proteins. Complement 1q (C1q) proteins are TNF-related proteins in that crystollographic studies have revealed that TNF and the globular gC1q domain of mouse ACRP30 have a closely related tertiary structure and trimeric organization suggestive of an evolutionary link between the TNF and C1q families. The human C1q gene family comprises, to date, of 13 members, including collagenous members such as CRF, ACRP30, CORS26, EMILIN-1, EMILIN-2, collagens VII and X, and non-collagenous members such as precerebellin and multimerin. ACRP30 is an abundant serum protein, synthesized in adipose tissue in response to insulin, and is down-regulated in the obese mouse and humans. For a recent review of the C1q family, see Bodmer et al., (2002), TRENDS in Biochemical Sciences 27(1):19-26.

C1q family members may be useful for the treatment, prevention and/or diagnosis of medical conditions and diseases such as cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogenesis disorder, Kaposis' sarcoma; autoimmune/inflammatory disorders, including allergy, inflammatory bowel disease, arthritis, psoriasis and respiratory tract inflammation, asthma, and organ transplant rejection; cardiovascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain;

developmental disorders; metabolic disorders including diabetes mellitus, osteoporosis, and obesity, AIDS and renal disease; infections including viral infection, bacterial infection, fungal infection and parasitic infection; and other disorders mediated by TNF-like secreted proteins, particularly those mediated by C1q family proteins.

It is anticipated that the INSP058 polypeptide is encoded by three exons (exon 1 encoding a polypeptide having the sequence recited in SEQ ID NO:2, exon 2 encoding a polypeptide having the sequence recited SEQ ID NO:4 and exon 3 encoding a polypeptide having the sequence SEQ ID NO:6). A sequence of some similarity to SEQ ID NO:8 has been disclosed in the prior art, although the protein was not annotated as a secreted protein with a TNF-like fold. This polypeptide sequence, presented in SEQ ID NO:8 of International patent application WO00/68380, is explicitly excluded from the scope of this aspect of the present invention.

The polypeptide having the sequence recited in SEQ ID NO:10 is referred to hereafter as the "INSP058SV polypeptide" or "INSP058SV". The INSP0158SV polypeptide is a splice variant of the INSP058 polypeptide, caused by a deletion in the central portion of exon 3 (SEQ ID NO:5). The deletion, as well as deleting a portion of exon 3, introduces a frameshift into the nucleotide sequence, the result being an early stop codon, so that the translated INSP058SV polypeptide is much shorter in length than the INSP058 polypeptide (FIG. 10). The INSP058SV protein lacks a domain matching the C1q domain that is found in the full length INSP058, suggesting that INSP058SV may be an antagonist of INSP058, acting, for example, to compete with the INSP058 version of the polypeptide for the same binding site on the receptor. In such a mechanism, the INSP058SV polypeptide would not stimulate the receptor, so that the normal biological effect would not be induced. Such a polypeptide would therefore be a competitive inhibitor of the natural polypeptide. Although the Applicant does not wish to be bound by this theory, it is postulated that the first 15 amino acids of INSP058 polypeptide and INSP058SV polypeptide each form a signal peptide.

The full length INSP058 polypeptide sequence without this postulated signal sequence is recited in SEQ ID NO: 14.

The polypeptide having the sequence recited in SEQ ID NO:14 is referred to hereafter as the "INSP058 mature polypeptide".

The term "INSP058 polypeptides" as used herein includes polypeptides comprising the INSP058 exon 1 polypeptide, the INSP058 exon 2 polypeptide, the INSP058 exon 3 polypeptide, the INSP058 polypeptide and the INSP058 mature polypeptide.

The full length INSP058SV polypeptide sequence without this postulated signal sequence is recited in SEQ ID NO:16.

The polypeptide having the sequence recited in SEQ ID NO:16 is referred to hereafter as the "INSP058SV mature polypeptide".

The term "INSP058SV polypeptides" as used herein includes polypeptides comprising the the INSP058SV mature polypeptide.

In a second aspect, the invention provides a purified nucleic acid molecule which encodes a polypeptide of the first aspect of the invention.

Preferably, the purified nucleic acid molecule comprises the nucleic acid sequence as recited in SEQ ID NO:7 (encoding the INSP058 polypeptide), SEQ ID NO:9 (encoding the INSP058SV polypeptide), SEQ ID NO:11 (encoding the exon 1 polypeptide of mature INSP058), SEQ ID NO:13 (encoding the mature INSP058 polypeptide), SEQ ID NO:15 (encoding the mature INSP058SV polypeptide), or is a redundant equivalent or fragment of this sequence.

The invention further provides that the purified nucleic acid molecule consists of the nucleic acid sequence as recited in SEQ ID NO:7, SEQ ID NO:9 (encoding the INSP058SV polypeptide), SEQ ID NO:11 (encoding the exon 1 polypeptide of mature INSP058 or mature INSP058SV), SEQ ID NO:13 (encoding the mature INSP058 polypeptide), SEQ ID NO:15 (encoding the mature INSP058SV polypeptide), or is a redundant equivalent or fragment of this sequence.

In a third aspect, the invention provides a purified nucleic acid molecule which hybridizes under high stringency conditions with a nucleic acid molecule of the second aspect of the invention.

In a fourth aspect, the invention provides a vector, such as an expression vector, that contains a nucleic acid molecule of the second or third aspect of the invention.

In a fifth aspect, the invention provides a host cell transformed with a vector of the fourth aspect of the invention.

In a sixth aspect, the invention provides a ligand that binds specifically to the polypeptide of the first aspect of the invention. Preferably, the ligand inhibits the function of a polypeptide of the first aspect of the invention which is a secreted protein with a TNF-like activity. Ligands to a polypeptide according to the invention may come in various forms, including natural or modified substrates, enzymes, receptors, small organic molecules such as small natural or synthetic organic molecules of up to 2000D, preferably 800D or lesss, peptidomimetics, inorganic molecules, peptides, polypeptides, antibodies, structural or functional mimetics of the aforementioned.

In a seventh aspect, the invention provides a compound that is effective to alter the expression of a natural gene which encodes a polypeptide of the first aspect of the invention or to regulate the activity of a polypeptide of the first aspect of the invention.

A compound of the seventh aspect of the invention may either increase (agonise) or decrease (antagonise) the level of expression of the gene or the activity of the polypeptide. Importantly, the identification of the function of the INSP058 allows for the design of screening methods capable of identifying compounds that are effective in the treatment and/or diagnosis of disease. Ligands and compounds according to the sixth and seventh aspects of the invention may be identified using such methods. These methods are included as aspects of the present invention.

In an eighth aspect, the invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in therapy or diagnosis of diseases in which TNF-like secreted proteins are implicated. Such diseases may include, but are not limited to, cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogenesis disorder, Kaposis' sarcoma; autoimmune/inflammatory disorders, including allergy, inflammatory bowel disease, arthritis; psoriasis and respiratory tract inflammation, asthma, and organ transplant rejection; cardiovascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain;

developmental disorders; metabolic disorders including diabetes mellitus, osteoporosis, and obesity, AIDS and renal disease; infections including viral infection, bacterial infection, fungal infection and parasitic infection; and other disorders mediated by TNF-like secreted proteins, particularly those mediated by C1q family proteins. These molecules may also be used in the manufacture of a medicament for the treatment such diseases. The moieties of the first, second, third, fourth, fifth, sixth or seventh aspect of the invention may also be used in the manufacture of a medicament for the treatment of such diseases.

In a ninth aspect, the invention provides a method of diagnosing a disease in a patient, comprising assessing the level of expression of a natural gene encoding a polypeptide of the first aspect of the invention or the activity of a polypeptide of the first aspect of the invention in tissue from said patient and comparing said level of expression or activity to a control level, wherein a level that is different to said control level is indicative of disease. Such a method will preferably be carried out in vitro. Similar methods may be used for monitoring the therapeutic treatment of disease in a patient, wherein altering the level of expression or activity of a polypeptide or nucleic acid molecule over the period of time towards a control level is indicative of regression of disease.

A preferred method for detecting polypeptides of the first aspect of the invention comprises the steps of: (a) contacting a ligand, such as an antibody, of the sixth aspect of the invention with a biological sample under conditions suitable for the formation of a ligand-polypeptide complex; and (b) detecting said complex.

A number of different such methods according to the ninth aspect of the invention exist, as the skilled reader will be aware, such as methods of nucleic acid hybridization with short probes, point mutation analysis, polymerase chain reaction (PCR) amplification and methods using antibodies to detect aberrant protein levels. Similar methods may be used on a short or long term basis to allow therapeutic treatment of a disease to be monitored in a patient. The invention also provides kits that are useful in these methods for diagnosing disease.

Preferably, the disease diagnosed by a method of the ninth aspect of the invention is a disease in which a TNF-like secreted protein is implicated, as described above.

In a tenth aspect, the invention provides for the use of a polypeptide of the first aspect of the invention as a TNF-like secreted protein.

In an eleventh aspect, the invention provides a pharmaceutical composition comprising a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, in conjunction with a pharmaceutically-acceptable carrier.

In a twelfth aspect, the present invention provides a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention, for use in the manufacture of a medicament for the diagnosis or treatment of a disease.

Preferably, the disease is a disease in which TNF-like secreted proteins are implicated, as described above.

In a thirteenth aspect, the invention provides a method of treating a disease in a patient comprising administering to the patient a polypeptide of the first aspect of the invention, or a nucleic acid molecule of the second or third aspect of the invention, or a vector of the fourth aspect of the invention, or a host cell of the fifth aspect of the invention, or a ligand of the sixth aspect of the invention, or a compound of the seventh aspect of the invention.

For diseases in which the expression of a natural gene encoding a polypeptide of the first aspect of the invention, or in which the activity of a polypeptide of the first aspect of the invention, is lower in a diseased patient when compared to the level of expression or activity in a healthy patient, the polypeptide, nucleic acid molecule, vector, host cell, ligand or compound administered to the patient should be an agonist. Conversely, for diseases in which the expression of the natural gene or activity of the polypeptide is higher in a diseased patient when compared to the level of expression or activity in a healthy patient, the polypeptide, nucleic acid molecule, vector, host cell, ligand or compound administered to the patient should be an antagonist. Examples of such antagonists include antisense nucleic acid molecules, ribozymes and ligands, such as antibodies.

Preferably, the disease is a disease in which a TNF-like secreted protein is implicated, as described above.

In a fourteenth aspect, the invention provides transgenic or knockout non-human animals that have been transformed to express higher, lower or absent levels of a polypeptide of the first aspect of the invention. Such transgenic animals are very useful models for the study of disease and may also be used in screening regimes for the identification of compounds that are effective in the treatment or diagnosis of such a disease.

A summary of standard techniques and procedures which may be employed in order to utilise the invention is given below. It will be understood that this invention is not limited to the particular methodology, protocols, cell lines, vectors and reagents described. It is also to be understood that the terminology used herein is for the purpose of describing particular embodiments only and it is not intended that this terminology should limit the scope of the present invention. The extent of the invention is limited only by the terms of the appended claims.

Standard abbreviations for nucleotides and amino acids are used in this specification.

The practice of the present invention will employ, unless otherwise indicated, conventional techniques of molecular biology, microbiology, recombinant DNA technology and immunology, which are within the skill of those working in the art.

Such techniques are explained fully in the literature. Examples of particularly suitable texts for consultation include the following: Molecular Cloning; A Laboratory Manual, Third Edition (Sambrook ed. 2001); DNA Cloning, Volumes I and II (D. N Glover ed. 1985); Oligonucleotide Synthesis (M. J. Gait ed. 1984); Nucleic Acid Hybridization (B. D. Hames & S. J. Higgins eds. 1984); Transcription and Translation (B. D. Hames & S. J. Higgins eds. 1984); Animal Cell Culture (R. I. Freshney ed. 1986); Immobilized Cells and Enzymes (IRL Press, 1986); B. Perbal, A Practical Guide to Molecular Cloning (1984); the Methods in Enzymology series (Academic Press, Inc.), especially volumes 154 & 155; Gene Transfer Vectors for Mammalian Cells (J. H. Miller and M. P. Calos eds. 1987, Cold Spring Harbor Laboratory); Immunochemical Methods in Cell and Molecular Biology (Mayer and Walker, eds. 1987, Academic Press, London); Scopes, (1987) Protein Purification: Principles and Practice, Second Edition (Springer Verlag, N.Y.); and Handbook of Experimental Immunology, Volumes I-IV (D. M. Weir and C. C. Blackwell eds. 1986).

As used herein, the term "polypeptide" includes any peptide or protein comprising two or more amino acids joined to each other by peptide bonds or modified peptide bonds, i.e. peptide isosteres. This term refers both to short chains (peptides and oligopeptides) and to longer chains (proteins).

The polypeptide of the present invention may be in the form of a mature protein or may be a pre-, pro- or prepro-protein that can be activated by cleavage of the pre-, pro- or prepro-portion to produce an active mature polypeptide. In such polypeptides, the pre-, pro- or prepro-sequence may be a leader or secretory sequence or may be a sequence that is employed for purification of the mature polypeptide sequence.

The polypeptide of the first aspect of the invention may form part of a fusion protein. For example, it is often advantageous to include one or more additional amino acid sequences which may contain secretory or leader sequences, pro-sequences, sequences which aid in purification, or sequences that confer higher protein stability, for example during recombinant production. Alternatively or additionally, the mature polypeptide may be fused with another compound, such as a compound to increase the half-life of the polypeptide (for example, polyethylene glycol).

Polypeptides may contain amino acids other than the 20 gene-encoded amino acids, modified either by natural processes, such as by post-translational processing or by chemical modification techniques which are well known in the art. Among the known modifications which may commonly be present in polypeptides of the present invention are glycosylation, lipid attachment, sulphation, gamma-carboxylation, for instance of glutamic acid residues, hydroxylation and ADP-ribosylation. Other potential modifications include acetylation, acylation, amidation, covalent attachment of flavin, covalent attachment of a haeme moiety, covalent attachment of a nucleotide or nucleotide derivative, covalent attachment of a lipid derivative, covalent attachment of phosphatidylinositol, cross-linking, cyclization, disulphide bond formation, demethylation, formation of covalent cross-links, formation of cysteine, formation of pyroglutamate, formylation, GPI anchor formation, iodination, methylation, myristoylation, oxidation, proteolytic processing, phosphorylation, prenylation, racemization, selenoylation, transfer-RNA mediated addition of amino acids to proteins such as arginylation, and ubiquitination.

Modifications can occur anywhere in a polypeptide, including the peptide backbone, the amino acid side-chains and the amino or carboxyl termini. In fact, blockage of the amino or carboxyl terminus in a polypeptide, or both, by a covalent modification is common in naturally-occurring and synthetic polypeptides and such modifications may be present in polypeptides of the present invention.

The modifications that occur in a polypeptide often will be a function of how the polypeptide is made. For polypeptides that are made recombinantly, the nature and extent of the modifications in large part will be determined by the post-translational modification capacity of the particular host cell and the modification signals that are present in the amino acid sequence of the polypeptide in question. For instance, glycosylation patterns vary between different types of host cell.

The polypeptides of the present invention can be prepared in any suitable manner. Such polypeptides include isolated naturally-occurring polypeptides (for example purified from cell culture), recombinantly-produced polypeptides (including fusion proteins), synthetically-produced polypeptides or polypeptides that are produced by a combination of these methods.

The functionally-equivalent polypeptides of the first aspect of the invention may be polypeptides that are homologous to the INSP058 polypeptide. Two polypeptides are said to be "homologous", as the term is used herein, if the sequence of one of the polypeptides has a high enough degree of identity or similarity to the sequence of the other polypeptide. "Identity" indicates that at any particular position in the aligned sequences, the amino acid residue is identical between the sequences. "Similarity" indicates that, at any particular position in the aligned sequences, the amino acid residue is of a similar type between the sequences. Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Homologous polypeptides therefore include natural biological variants (for example, allelic variants or geographical variations within the species from which the polypeptides are derived) and mutants (such as mutants containing amino acid substitutions, insertions or deletions) of the INSP058 polypeptide. Such mutants may include polypeptides in which one or more of the amino acid residues are substituted with a conserved or non-conserved amino acid residue (preferably a conserved amino acid residue) and such substituted amino acid residue may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 5 and 10, 1 and 5, 1 and 3, 1 and 2 or just 1 amino acids are substituted, deleted or added in any combination. Especially preferred are silent substitutions, additions and deletions, which do not alter the properties and activities of the protein. Also especially preferred in this regard are conservative substitutions. Such mutants also include polypeptides in which one or more of the amino acid residues includes a substituent group.

Typically, greater than 30% identity between two polypeptides is considered to be an indication of functional equivalence. Preferably, functionally equivalent polypeptides of the first aspect of the invention have a degree of sequence identity with the INSP058 polypeptide, or with active fragments thereof, of greater than 80%. More preferred polypeptides of the present invention have degrees of identity of greater than 85%, 90%, 95%, 98% or 99%, respectively to INSP058 polypeptide.

The functionally-equivalent polypeptides of the first aspect of the invention may also be polypeptides which have been identified using one or more techniques of structural alignment. For example, the Inpharmatica Genome Threader technology that forms one aspect of the search tools used to generate the Biopendium search database may be used (see co-pending International Patent Application PCT/GB01/01105) to identify polypeptides of presently-unknown function which, while having low sequence identity as compared to the INSP058 polypeptide, are predicted to have the function of a TNF-like secreted protein, by virtue of sharing significant structural homology with the INSP058 polypeptide. By "significant structural homology" is meant that the Inpharmatica Genome Threader predicts two proteins to share structural homology with a certainty of 10% and above.

The polypeptides of the first aspect of the invention also include fragments of the INSP058 polypeptide and fragments of the functional equivalents of the INSP058 polypeptide, provided that those fragments retain the function of a TNF-like secreted protein or have an antigenic determinant in common with the INSP058 polypeptide.

As used herein, the term "fragment" refers to a polypeptide having an amino acid sequence that is the same as part, but not all, of the amino acid sequence of the INSP058 polypeptide, or one of their functional equivalents. The fragments should comprise at least n consecutive amino acids from the sequence and, depending on the particular sequence, n preferably is 7 or more (for example, 8, 10, 12, 14, 16, 18, 20 or more). Small fragments may form an antigenic determinant.

Fragments of the full length INSP058 polypeptide may consist of combinations of 1 or more of neighbouring exon sequences or even combinations of partial exon sequences. For example, such combinations may include exons 1, 2 and the partial sequence of exon 3 of the INSP058 polypeptide, as is the case with INSP058 SV.

Such fragments may be "free-standing", i.e. not part of or fused to other amino acids or polypeptides, or they may be comprised within a larger polypeptide of which they form a part or region. When comprised within a larger polypeptide, the fragment of the invention most preferably forms a single continuous region. For instance, certain preferred embodiments relate to a fragment having a pre- and/or pro-polypeptide region fused to the amino terminus of the fragment and/or an additional region fused to the carboxyl terminus of the fragment. However, several fragments may be comprised within a single larger polypeptide.

The polypeptides of the present invention or their immunogenic fragments (comprising at least one antigenic determinant) can be used to generate ligands, such as polyclonal or monoclonal antibodies, that are immunospecific for the polypeptides. Such antibodies may be employed to isolate or to identify clones expressing the polypeptides of the invention or to purify the polypeptides by affinity chromatography. The antibodies may also be employed as diagnostic or therapeutic aids, amongst other applications, as will be apparent to the skilled reader.

The term "immunospecific" means that the antibodies have substantially greater affinity for the polypeptides of the invention than their affinity for other related polypeptides in the prior art. As used herein, the term "antibody" refers to intact molecules as well as to fragments thereof, such as Fab, F(ab')2 and Fv, which are capable of binding to the antigenic determinant in question. Such antibodies thus bind to the polypeptides of the first aspect of the invention.

By "substantially greater affinity" we mean that there is a measurable increase in the affinity for a polypeptide of the invention as compared with the affinity for known cell-surface receptors.

Preferably, the affinity is at least 1.5-fold, 2-fold, 5-fold 10-fold, 100-fold, $10^3$-fold, $10^4$-fold, $10^5$-fold or $10^6$-fold greater for a polypeptide of the invention than for known cell-surface receptor polypeptides.

If polyclonal antibodies are desired, a selected mammal, such as a mouse, rabbit, goat or horse, may be immunised with a polypeptide of the first aspect of the invention. The polypeptide used to immunise the animal can be derived by recombinant DNA technology or can be synthesized chemically. If desired, the polypeptide can be conjugated to a carrier protein. Commonly used carriers to which the polypeptides may be chemically coupled include bovine serum albumin, thyroglobulin and keyhole limpet haemocyanin. The coupled polypeptide is then used to immunise the animal. Serum from the immunised animal is collected and treated according to known procedures, for example by immunoaffinity chromatography.

Monoclonal antibodies to the polypeptides of the first aspect of the invention can also be readily produced by one skilled in the art. The general methodology for making monoclonal antibodies using hybridoma technology is well known (see, for example, Kohler, G. and Milstein, C., Nature 256: 495-497 (1975); Kozbor et al., Immunology Today 4: 72 (1983); Cole et al., 77-96 in Monoclonal Antibodies and Cancer Therapy, Alan R. Liss, Inc. (1985).

Panels of monoclonal antibodies produced against the polypeptides of the first aspect of the invention can be screened for various properties, i.e., for isotype, epitope, affinity, etc. Monoclonal antibodies are particularly useful in purification of the individual polypeptides against which they are directed. Alternatively, genes encoding the monoclonal antibodies of interest may be isolated from hybridomas, for instance by PCR techniques known in the art, and cloned and expressed in appropriate vectors.

Chimeric antibodies, in which non-human variable regions are joined or fused to human constant regions (see, for example, Liu et al., Proc. Natl. Acad. Sci. USA, 84, 3439 (1987)), may also be of use.

The antibody may be modified to make it less immunogenic in an individual, for example by humanisation (see Jones et al., Nature, 321, 522 (1986); Verhoeyen et al., Science, 239, 1534 (1988); Kabat et al., J. Immunol., 147, 1709 (1991); Queen et al., Proc. Natl. Acad. Sci. USA, 86, 10029 (1989); Gorman et al., Proc. Natl. Acad. Sci. USA, 88, 34181 (1991); and Hodgson et al., Bio/Technology, 9, 421 (1991)). The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody.

In a further alternative, the antibody may be a "bispecific" antibody, that is an antibody having two different antigen binding domains, each domain being directed against a different epitope.

Phage display technology may be utilised to select genes which encode antibodies with binding activities towards the polypeptides of the invention either from repertoires of PCR amplified V-genes of lymphocytes from humans screened for possessing the relevant antibodies, or from naive libraries (McCafferty, J. et al., (1990), Nature 348, 552-554; Marks, J. et al., (1992) Biotechnology 10, 779-783). The affinity of these antibodies can also be improved by chain shuffling (Clackson, T. et al., (1991) Nature 352, 624-628).

Antibodies generated by the above techniques, whether polyclonal or monoclonal, have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme.

Preferred nucleic acid molecules of the second and third aspects of the invention are those which encode the polypeptide sequence recited in SEQ ID NO:8 and functionally equivalent polypeptides. These nucleic acid molecules may be used in the methods and applications described herein. The nucleic acid molecules of the invention preferably comprise at least n consecutive nucleotides from the sequences disclosed herein where, depending on the particular sequence, n is 10 or more (for example, 12, 14, 15, 18, 20, 25, 30, 35, 40 or more).

The nucleic acid molecules of the invention also include sequences that are complementary to nucleic acid molecules described above (for example, for antisense or probing purposes).

Nucleic acid molecules of the present invention may be in the form of RNA, such as mRNA, or in the form of DNA, including, for instance cDNA, synthetic DNA or genomic DNA. Such nucleic acid molecules may be obtained by cloning, by chemical synthetic techniques or by a combination thereof. The nucleic acid molecules can be prepared, for example, by chemical synthesis using techniques such as solid phase phosphoramidite chemical synthesis, from genomic or cDNA libraries or by separation from an organism. RNA molecules may generally be generated by the in vitro or in vivo transcription of DNA sequences.

The nucleic acid molecules may be double-stranded or single-stranded. Single-stranded DNA may be the coding strand, also known as the sense strand, or it may be the non-coding strand, also referred to as the anti-sense strand.

The term "nucleic acid molecule" also includes analogues of DNA and RNA, such as those containing modified backbones, and peptide nucleic acids (PNA). The term "PNA", as used herein, refers to an antisense molecule or an anti-gene agent which comprises an oligonucleotide of at least five nucleotides in length linked to a peptide backbone of amino acid residues, which preferably ends in lysine. The terminal lysine confers solubility to the composition. PNAs may be pegylated to extend their lifespan in a cell, where they preferentially bind complementary single stranded DNA and RNA and stop transcript elongation (Nielsen, P. E. et al., (1993) Anticancer Drug Des. 8:53-63).

A nucleic acid molecule which encodes the polypeptide of SEQ ID NO:8, may be identical to the coding sequence of the nucleic acid molecule shown in SEQ ID NO:7.

These molecules also may have a different sequence which, as a result of the degeneracy of the genetic code, encodes a polypeptide of SEQ ID NO:8. Such nucleic acid molecules may include, but are not limited to, the coding sequence for the mature polypeptide by itself; the coding sequence for the mature polypeptide and additional coding sequences, such as those encoding a leader or secretory sequence, such as a pro-, pre- or prepro-polypeptide sequence; the coding sequence of the mature polypeptide, with or without the aforementioned additional coding sequences, together with further additional, non-coding sequences, including non-coding 5' and 3' sequences, such as the transcribed, non-translated sequences that play a role in transcription (including termination signals), ribosome binding and mRNA stability. The nucleic acid molecules may also include additional sequences which encode additional amino acids, such as those which provide additional functionalities.

The nucleic acid molecules of the second and third aspects of the invention may also encode the fragments or the functional equivalents of the polypeptides and fragments of the first aspect of the invention. Such a nucleic acid molecule may be a naturally-occurring variant such as a naturally-occurring allelic variant, or the molecule may be a variant that is not known to occur naturally. Such non-naturally occurring variants of the nucleic acid molecule may be made by mutagenesis techniques, including those applied to nucleic acid molecules, cells or organisms.

Among variants in this regard are variants that differ from the aforementioned nucleic acid molecules by nucleotide substitutions, deletions or insertions. The substitutions, deletions or insertions may involve one or more nucleotides. The variants may be altered in coding or non-coding regions or both. Alterations in the coding regions may produce conservative or non-conservative amino acid substitutions, deletions or insertions.

The nucleic acid molecules of the invention can also be engineered, using methods generally known in the art, for a variety of reasons, including modifying the cloning, processing, and/or expression of the gene product (the polypeptide). DNA shuffling by random fragmentation and PCR reassembly of gene fragments and synthetic oligonucleotides are included as techniques which may be used to engineer the nucleotide sequences. Site-directed mutagenesis may be used to insert new restriction sites, alter glycosylation patterns, change codon preference, produce splice variants, introduce mutations and so forth.

Nucleic acid molecules which encode a polypeptide of the first aspect of the invention may be ligated to a heterologous sequence so that the combined nucleic acid molecule encodes a fusion protein. Such combined nucleic acid molecules are included within the second or third aspects of the invention. For example, to screen peptide libraries for inhibitors of the activity of the polypeptide, it may be useful to express, using such a combined nucleic acid molecule, a fusion protein that can be recognised by a commercially-available antibody. A fusion protein may also be engineered to contain a cleavage site located between the sequence of the polypeptide of the invention and the sequence of a heterologous protein so that the polypeptide may be cleaved and purified away from the heterologous protein.

The nucleic acid molecules of the invention also include antisense molecules that are partially complementary to nucleic acid molecules encoding polypeptides of the present invention and that therefore hybridize to the encoding nucleic acid molecules (hybridization). Such antisense molecules, such as oligonucleotides, can be designed to recognise, specifically bind to and prevent transcription of a target nucleic acid encoding a polypeptide of the invention, as will be known by those of ordinary skill in the art (see, for example, Cohen, J. S., Trends in Pharm. Sci., 10, 435 (1989), Okano, J. Neurochem. 56, 560 (1991); O'Connor, J. Neurochem 56, 560 (1991); Lee et al., Nucleic Acids Res 6, 3073 (1979); Cooney et al., Science 241, 456 (1988); Dervan et al., Science 251, 1360 (1991).

The term "hybridization" as used here refers to the association of two nucleic acid molecules with one another by hydrogen bonding. Typically, one molecule will be fixed to a solid support and the other will be free in solution. Then, the two molecules may be placed in contact with one another under conditions that favour hydrogen bonding. Factors that affect this bonding include: the type and volume of solvent; reaction temperature; time of hybridization; agitation; agents to block the non-specific attachment of the liquid phase molecule to the solid support (Denhardt's reagent or BLOTTO); the concentration of the molecules; use of compounds to increase the rate of association of molecules (dextran sulphate or polyethylene glycol); and the stringency of the washing conditions following hybridization (see Sambrook et al., [supra]).

The inhibition of hybridization of a completely complementary molecule to a target molecule may be examiined using a hybridization assay, as known in the art (see, for example, Sambrook et al., [supra]). A substantially homologous molecule will then compete for and inhibit the binding of a completely homologous molecule to the target molecule under various conditions of stringency, as taught in Wahl, G.

M. and S. L. Berger (1987; Methods Enzymol. 152:399-407) and Kimmel, A. R. (1987; Methods Enzymol. 152:507-511).

"Stringency" refers to conditions in a hybridization reaction that favour the association of very similar molecules over association of molecules that differ. High stringency hybridisation conditions are defined as overnight incubation at 42° C. in a solution comprising 50% formamide, 5×SSC (150 mM NaCl, 15 mM trisodium citrate), 50 mM sodium phosphate (pH7.6), 5× Denhardts solution, 10% dextran sulphate, and 20 microgram/ml denatured, sheared salmon sperm DNA, followed by washing the filters in 0.1×SSC at approximately 65° C. Low stringency conditions involve the hybridisation reaction being carried out at 35° C. (see Sambrook et al., [supra]). Preferably, the conditions used for hybridization are those of high stringency.

Preferred embodiments of this aspect of the invention are nucleic acid molecules that are at least 70% identical over their entire length to a nucleic acid molecule encoding the INSP058 polypeptide (SEQ ID NO:8), and nucleic acid molecules that are substantially complementary to said nucleic acid molecules of this embodiment. Preferably, a nucleic acid molecule according to this aspect of the invention comprises a region that is at least 97% identical over its entire length to such coding sequences, or is a nucleic acid molecule that is complementary thereto. In this regard, nucleic acid molecules at least 98%, preferably at least 99% or more identical over their entire length to the same are particularly preferred. Preferred embodiments in this respect are nucleic acid molecules that encode polypeptides which retain substantially the same biological function or activity as the INSP058 polypeptide.

The invention also provides a process for detecting a nucleic acid molecule of the invention, comprising the steps of: (a) contacting a nucleic probe according to the invention with a biological sample under hybridizing conditions to form duplexes; and (b) detecting any such duplexes that are formed.

As discussed additionally below in connection with assays that may be utilised according to the invention, a nucleic acid molecule as described above may be used as a hybridization probe for RNA, cDNA or genomic DNA, in order to isolate full-length cDNAs and genomic clones encoding the INSP058 polypeptide and to isolate cDNA and genomic clones of homologous or orthologous genes that have a high sequence similarity to the gene encoding this polypeptide.

In this regard, the following techniques, among others known in the art, may be utilised and are discussed below for purposes of illustration. Methods for DNA sequencing and analysis are well known and are generally available in the art and may, indeed, be used to practice many of the embodiments of the invention discussed herein. Such methods may employ such enzymes as the Klenow fragment of DNA polymerase I, Sequenase (US Biochemical Corp, Cleveland, Ohio), Taq polymerase (Perkin Elmer), thermostable T7 polymerase (Amersham, Chicago, Ill.), or combinations of polymerases and proof-reading exonucleases such as those found in the ELONGASE Amplification System marketed by Gibco/BRL (Gaithersburg, Md.). Preferably, the sequencing process may be automated using machines such as the Hamilton Micro Lab 2200 (Hamilton, Reno, Nev.), the Peltier Thermal Cycler (PTC200; MJ Research, Watertown, Mass.) and the ABI Catalyst and 373 and 377 DNA Sequencers (Perkin Elmer).

One method for isolating a nucleic acid molecule encoding a polypeptide with an equivalent function to that of the INSP058 polypeptide is to probe a genomic or cDNA library with a natural or artificially-designed probe using standard procedures that are recognised in the art (see, for example, "Current Protocols in Molecular Biology", Ausubel et al., (eds). Greene Publishing Association and John Wiley Interscience, New York, 1989, 1992). Probes comprising at least 15, preferably at least 30, and more preferably at least 50, contiguous bases that correspond to, or are complementary to, nucleic acid sequences from the appropriate encoding gene (SEQ ID NO:7), are particularly useful probes. Such probes may be labelled with an analytically-detectable reagent to facilitate their identification. Useful reagents include, but are not limited to, radioisotopes, fluorescent dyes and enzymes that are capable of catalysing the formation of a detectable product. Using these probes, the ordinarily skilled artisan will be capable of isolating complementary copies of genomic DNA, cDNA or RNA polynucleotides encoding proteins of interest from human, mammalian or other animal sources and screening such sources for related sequences, for example, for additional members of the family, type and/or subtype.

In many cases, isolated cDNA sequences will be incomplete, in that the region encoding the polypeptide will be cut short, normally at the 5' end. Several methods are available to obtain full length cDNAs, or to extend short cDNAs. Such sequences may be extended utilising a partial nucleotide sequence and employing various methods known in the art to detect upstream sequences such as promoters and regulatory elements. For example, one method which may be employed is based on the method of Rapid Amplification of cDNA Ends (RACE; see, for example, Frohman et al., PNAS USA 85, 8998-9002, 1988). Recent modifications of this technique, exemplified by the Marathon™ technology (Clontech Laboratories Inc.), for example, have significantly simplified the search for longer cDNAs. A slightly different technique, termed "restriction-site" PCR, uses universal primers to retrieve unknown nucleic acid sequence adjacent a known locus (Sarkar, G. (1993) PCR Methods Applic. 2:318-322). Inverse PCR may also be used to amplify or to extend sequences using divergent primers based on a known region (Triglia, T. et al., (1988) Nucleic Acids Res. 16:8186). Another method which may be used is capture PCR which involves PCR amplification of DNA fragments adjacent a known sequence in human and yeast artificial chromosome DNA (Lagerstrom, M. et al., (1991) PCR Methods Applic., 1, 111-119). Another method which may be used to retrieve unknown sequences is that of Parker, J. D. et al., (1991); Nucleic Acids Res. 19:3055-3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

In one embodiment of the invention, the nucleic acid molecules of the present invention may be used for chromosome localisation. In this technique, a nucleic acid molecule is specifically targeted to, and can hybridize with, a particular location on an individual human chromosome. The mapping of relevant sequences to chromosomes according to the present invention is an important step in the confirmatory correlation of those sequences with the gene-associated disease. Once a sequence has been mapped to a precise chromosomal location, the physical position of the sequence on the chromosome can be correlated with genetic map data Such data are found in, for example, V. McKusick, Mendelian Inheritance in Man (available on-line through Johns Hopkins University Welch Medical Library). The relationships between genes and diseases that have been mapped to the same chromosomal region are then identified through linkage analysis (coinheritance of physically adjacent genes). This provides valuable information to investigators searching for disease genes using positional cloning or other gene discovery techniques. Once the disease or syndrome has been crudely localised by genetic linkage to a particular genomic region, any sequences mapping to that area may represent associated or regulatory genes for further investigation. The nucleic acid molecule may also be used to detect differences in the chromosomal location due to translocation, inversion, etc. among normal, carrier, or affected individuals.

The nucleic acid molecules of the present invention are also valuable for tissue localisation. Such techniques allow the determination of expression patterns of the polypeptide in tissues by detection of the mRNAs that encode them. These techniques include in situ hybridization techniques and nucleotide amplification techniques, such as PCR. Results from these studies provide an indication of the normal functions of the polypeptide in the organism. In addition, comparative studies of the normal expression pattern of mRNAs with that of mRNAs encoded by a mutant gene provide valuable insights into the role of mutant polypeptides in disease. Such inappropriate expression may be of a temporal, spatial or quantitative nature.

Gene silencing approaches may also be undertaken to down-regulate endogenous expression of a gene encoding a polypeptide of the invention. RNA interference (RNAi) (Elbashir, S M et al., Nature 2001, 411, 494-498) is one method of sequence specific post-transcriptional gene silencing that may be employed. Short dsRNA olignonucleotides are synthesised in vitro and introduced into a cell. The sequence specific binding of these dsRNA oligonucleotides triggers the degradation of target mRNA, reducing or ablating target protein expression.

Efficacy of the gene silencing approaches assessed above may be assessed through the measurement of polypeptide expression (for example, by Western blotting), and at the RNA level using TaqMan-based methodologies.

The vectors of the present invention comprise nucleic acid molecules of the invention and may be cloning or expression vectors. The host cells of the invention, which may be transformed, transfected or transduced with the vectors of the invention may be prokaryotic or eukaryotic.

The polypeptides of the invention may be prepared in recombinant form by expression of their encoding nucleic acid molecules in vectors contained within a host cell. Such expression methods are well known to those of skill in the art and many are described in detail by Sambrook et al., (supra) and Fernandez & Hoeffler (1998, eds. "Gene expression systems. Using nature for the art of expression". Academic Press, San Diego, London, Boston, New York, Sydney, Tokyo, Toronto).

Generally, any system or vector that is suitable to maintain, propagate or express nucleic acid molecules to produce a polypeptide in the required host may be used. The appropriate nucleotide sequence may be inserted into an expression system by any of a variety of well-known and routine techniques, such as, for example, those described in Sambrook et al., (supra). Generally, the encoding gene can be placed under the control of a control element such as a promoter, ribosome binding site (for bacterial expression) and, optionally, an operator, so that the DNA sequence encoding the desired polypeptide is transcribed into RNA in the transformed host cell.

Examples of suitable expression systems include, for example, chromosomal, episomal and virus-derived systems, including, for example, vectors derived from: bacterial plasmids, bacteriophage, transposons, yeast episomes, insertion elements, yeast chromosomal elements, viruses such as baculoviruses, papova viruses such as SV40, vaccinia viruses, adenoviruses, fowl pox viruses, pseudorabies viruses and retroviruses, or combinations thereof, such as those derived from plasmid and bacteriophage genetic elements, including cosmids and phagemids. Human artificial chromosomes (HACs) may also be employed to deliver larger fragments of DNA than can be contained and expressed in a plasmid.

Particularly suitable expression systems include microorganisms such as bacteria transformed with recombinant bacteriophage, plasmid or cosmid DNA expression vectors; yeast transformed with yeast expression vectors; insect cell systems infected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the polypeptides of the invention.

Introduction of nucleic acid molecules encoding a polypeptide of the present invention into host cells can be effected by methods described in many standard laboratory manuals, such as Davis et al., Basic Methods in Molecular Biology (1986) and Sambrook et al., [supra]. Particularly suitable methods include calcium phosphate transfection, DEAE-dextran mediated transfection, transfection, microinjection, cationic lipid-mediated transfection, electroporation, transduction, scrape loading, ballistic introduction or infection (see Sambrook et al., 1989 [supra]; Ausubel et al., 1991 [supra]; Spector, Goldman & Leinwald, 1998). In eukaryotic cells, expression systems may either be transient (for example, episomal) or permanent (chromosomal integration) according to the needs of the system.

The encoding nucleic acid molecule may or may not include a sequence encoding a control sequence, such as a signal peptide or leader sequence, as desired, for example, for secretion of the translated polypeptide into the lumen of the endoplasmic reticulum, into the periplasmic space or into the extracellular environment. These signals may be endogenous to the polypeptide or they may be heterologous signals. Leader sequences can be removed by the bacterial host in post-translational processing.

In addition to control sequences, it may be desirable to add regulatory sequences that allow for regulation of the expression of the polypeptide relative to the growth of the host cell. Examples of regulatory sequences are those which cause the expression of a gene to be increased or decreased in response to a chemical or physical stimulus, including the presence of a regulatory compound or to various temperature or metabolic conditions. Regulatory sequences are those non-translated regions of the vector, such as enhancers, promoters and 5' and 3' untranslated regions. These interact with host cellular proteins to carry out transcription and translation. Such regulatory sequences may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the Bluescript phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (for example, heat shock, RUBISCO and storage protein genes) or from plant viruses (for example, viral promoters or leader sequences) may be cloned into the vector. In mammalian cell systems, promoters from mammalian genes or from mammalian viruses are preferable. If it is necessary to generate a cell line that contains multiple copies of the sequence, vectors based on SV40 or EBV may be used with an appropriate selectable marker.

An expression vector is constructed so that the particular nucleic acid coding sequence is located in the vector with the appropriate regulatory sequences, the positioning and orientation of the coding sequence with respect to the regulatory sequences being such that the coding sequence is transcribed under the "control" of the regulatory sequences, i.e., RNA polymerase which binds to the DNA molecule at the control sequences transcribes the coding sequence. In some cases it may be necessary to modify the sequence so that it may be attached to the control sequences with the appropriate orientation; i.e., to maintain the reading frame.

The control sequences and other regulatory sequences may be ligated to the nucleic acid coding sequence prior to insertion into a vector. Alternatively, the coding sequence can be cloned directly into an expression vector that already contains the control sequences and an appropriate restriction site.

For long-term, high-yield production of a recombinant polypeptide, stable expression is preferred. For example, cell lines which stably express the polypeptide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (B3HK), monkey kidney (COS), C127, 3T3, BHK, HEK 293, Bowes melanoma and human hepatocellular carcinoma (for example Hep G2) cells and a number of other cell lines.

In the baculovirus system, the materials for baculovirus/insect cell expression systems are commercially available in kit form from, inter alia, Invitrogen, San Diego Calif. (the "MaxBac" kit). These techniques are generally known to those skilled in the art and are described fully in Summers and Smith, Texas Agricultural Experiment Station Bulletin No. 1555 (1987). Particularly suitable host cells for use in this system include insect cells such as *Drosophila* S2 and *Spodoptera* Sf9 cells.

There are many plant cell culture and whole plant genetic expression systems known in the art. Examples of suitable plant cellular genetic expression systems include those described in U.S. Pat. Nos. 5,693,506; 5,659,122; and 5,608,143. Additional examples of genetic expression in plant cell culture has been described by Zenk, Phytochemistry 30:3861-3863 (1991).

In particular, all plants from which protoplasts can be isolated and cultured to give whole regenerated plants can be utilised, so that whole plants are recovered which contain the transferred gene. Practically all plants can be regenerated from cultured cells or tissues, including but not limited to all major species of sugar cane, sugar beet, cotton, fruit and other trees, legumes and vegetables.

Examples of particularly preferred bacterial host cells include *streptococci, staphylococci, E. coli, Streptomyces* and *Bacillus subtilis* cells.

Examples of particularly suitable host cells for fungal expression include yeast cells (for example, *S. cerevisiae*) and *Aspergillus* cells.

Any number of selection systems are known in the art that may be used to recover transformed cell lines. Examples include the herpes simplex virus thymidine kinase (Wigler, M. et al., (1977) Cell 11:223-32) and adenine phosphoribosyltransferase (Lowy, I. et al., (1980) Cell 22:817-23) genes that can be employed in tk$^-$ or aprt$^±$ cells, respectively.

Also, antimetabolite, antibiotic or herbicide resistance can be used as the basis for selection; for example, dihydrofolate reductase (DHFR) that confers resistance to methotrexate (Wigler, M. et al., (1980) Proc. Natl. Acad. Sci. 77:3567-70); npt, which confers resistance to the aminoglycosides neomycin and G418 (Colbere-Garapin, F. et al., (1981) J. Mol. Biol. 150:1-14) and als or pat, which confer resistance to chlorsulfuron and phosphinotricin acetyltransferase, respectively. Additional selectable genes have been described, examples of which will be clear to those of skill in the art.

Although the presence or absence of marker gene expression suggests that the gene of interest is also present, its presence and expression may need to be confirmed. For example, if the relevant sequence is inserted within a marker gene sequence, transformed cells containing the appropriate sequences can be identified by the absence of marker gene function. Alternatively, a marker gene can be placed in tandem with a sequence encoding a polypeptide of the invention under the control of a single promoter. Expression of the marker gene in response to induction or selection usually indicates expression of the tandem gene as well.

Alternatively, host cells that contain a nucleic acid sequence encoding a polypeptide of the invention and which express said polypeptide may be identified by a variety of procedures known to those of skill in the art. These procedures include, but are not limited to, DNA-DNA or DNA-RNA hybridizations and protein bioassays, for example, fluorescence activated cell sorting (FACS) or immunoassay techniques (such as the enzyme-linked immunosorbent assay [ELISA] and radioimmunoassay [RIA]), that include membrane, solution, or chip based technologies for the detection and/or quantification of nucleic acid or protein (see Hampton, R. et al., (1990) Serological Methods, a Laboratory Manual, APS Press, St Paul, Minn.) and Maddox, D. E. et al., (1983) J. Exp. Med, 158, 1211-1216).

A wide variety of labels and conjugation techniques are known by those skilled in the art and may be used in various nucleic acid and amino acid assays. Means for producing labelled hybridization or PCR probes for detecting sequences related to nucleic acid molecules encoding polypeptides of the present invention include oligolabelling, nick translation, end-labelling or PCR amplification using a labelled polynucleotide. Alternatively, the sequences encoding the polypeptide of the invention may be cloned into a vector for the production of an mRNA probe. Such vectors are known in the art, are commercially available, and may be used to synthesise RNA probes in vitro by addition of an appropriate RNA polymerase such as T7, T3 or SP6 and labelled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio)).

Suitable reporter molecules or labels, which may be used for ease of detection, include radionuclides, enzymes and fluorescent, chemiluminescent or chromogenic agents as well as substrates, cofactors, inhibitors, magnetic particles, and the like.

Nucleic acid molecules according to the present invention may also be used to create transgenic animals, particularly rodent animals. Such transgenic animals form a further aspect of the present invention. This may be done locally by modification of somatic cells, or by germ line therapy to incorporate heritable modifications. Such transgenic animals may be particularly useful in the generation of animal models for drug molecules effective as modulators of the polypeptides of the present invention.

The polypeptide can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography is particularly useful for purification. Well known techniques for refolding proteins may be employed to regenerate an active conformation when the polypeptide is denatured during isolation and or purification.

Specialised vector constructions may also be used to facilitate purification of proteins, as desired, by joining sequences encoding the polypeptides of the invention to a nucleotide sequence encoding a polypeptide domain that will facilitate purification of soluble proteins. Examples of such purification-facilitating domains include metal chelating peptides such as histidine-tryptophan modules that allow purification on immobilised metals, protein A domains that allow purification on immobilised immunoglobulin, and the domain utilised in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the polypeptide of the invention may be used to facilitate purification. One such expression vector provides for expression of a fusion protein containing the polypeptide of the invention fused to several histidine residues preceding a thioredoxin or an enterokinase cleavage site. The histidine residues facilitate purification by IMAC (immobilised metal ion affinity chromatography as described in Porath, J. et al., (1992), Prot. Exp. Purif. 3: 263-281) while the thioredoxin or enterokinase cleavage site provides a means for purifying the polypeptide from the fusion protein. A discussion of vectors which contain fusion proteins is provided in Kroll, D. J. et al., (1993; DNA Cell Biol. 12:441-453).

If the polypeptide is to be expressed for use in screening assays, generally it is preferred that it be produced at the surface of the host cell in which it is expressed. In this event, the host cells may be harvested prior to use in the screening assay, for example using techniques such as fluorescence activated cell sorting (FACS) or immunoaffinity techniques. If the polypeptide is secreted into the medium, the medium can be recovered in order to recover and purify the expressed polypeptide. If polypeptide is produced intracellularly, the cells must first be lysed before the polypeptide is recovered.

The polypeptide of the invention can be used to screen libraries of compounds in any of a variety of drug screening techniques. Such compounds may activate (agonise) or inhibit (antagonise) the level of expression of the gene or the activity of the polypeptide of the invention and form a further aspect of the present invention. Preferred compounds are effective to alter the expression of a natural gene which encodes a polypeptide of the first aspect of the invention or to regulate the activity of a polypeptide of the first aspect of the invention.

Agonist or antagonist compounds may be isolated from, for example, cells, cell-free preparations, chemical libraries or natural product mixtures. These agonists or antagonists may be natural or modified substrates, ligands, enzymes, receptors or structural or functional mimetics. For a suitable review of such screening techniques, see Coligan et al, Current Protocols in Immunology 1(2):Chapter 5 (1991).

Compounds that are most likely to be good antagonists are molecules that bind to the polypeptide of the invention without inducing the biological effects of the polypeptide upon binding to it. Potential antagonists include small organic molecules, peptides, polypeptides and antibodies that bind to the polypeptide of the invention and thereby inhibit or extinguish its activity. In this fashion, binding of the polypeptide to normal cellular binding molecules may be inhibited, such that the normal biological activity of the polypeptide is prevented.

The polypeptide of the invention that is employed in such a screening technique may be free in solution, affixed to a solid support, borne on a cell surface or located intracellularly. In general, such screening procedures may involve using appropriate cells or cell membranes that express the polypeptide that are contacted with a test compound to observe binding, or stimulation or inhibition of a functional response. The functional response of the cells contacted with the test compound is then compared with control cells that were not contacted with the test compound. Such an assay may assess whether the test compound results in a signal generated by activation of the polypeptide, using an appropriate detection system. Inhibitors of activation are generally assayed in the presence of a known agonist and the effect on activation by the agonist in the presence of the test compound is observed.

A preferred method for identifying an agonist or antagonist compound of a polypeptide of the present invention comprises:

(a) contacting a cell expressing on the surface thereof the polypeptide according to the first aspect of the invention, the polypeptide being associated with a second component capable of providing a detectable signal in response to the binding of a compound to the polypeptide, with a compound to be screened under conditions to permit binding to the polypeptide; and (b) determining whether the compound binds to and activates or inhibits the polypeptide by measuring the level of a signal generated from the interaction of the compound with the polypeptide.

A further preferred method for identifying an agonist or antagonist of a polypeptide of the invention comprises:

(a) contacting a cell expressing on the surface thereof the polypeptide, the polypeptide being associated with a second component capable of providing a detectable signal in response to the binding of a compound to the polypeptide, with a compound to be screened under conditions to permit binding to the polypeptide; and (b) determining whether the compound binds to and activates or inhibits the polypeptide by comparing the level of a signal generated from the interaction of the compound with the polypeptide with the level of a signal in the absence of the compound.

In further preferred embodiments, the general methods that are described above may further comprise conducting the identification of agonist or antagonist in the presence of labelled or unlabelled ligand for the polypeptide.

In another embodiment of the method for identifying an agonist or antagonist of a polypeptide of the present invention comprises:

determining the inhibition of binding of a ligand to cells which have a polypeptide of the invention on the surface thereof, or to cell membranes containing such a polypeptide, in the presence of a candidate compound under conditions to permit binding to the polypeptide, and determining the amount of ligand bound to the polypeptide. A compound capable of causing reduction of binding of a ligand is considered to be an agonist or antagonist. Preferably the ligand is labelled.

More particularly, a method of screening for a polypeptide antagonist or agonist compound comprises the steps of:
(a) incubating a labelled ligand with a whole cell expressing a polypeptide according to the invention on the cell surface, or a cell membrane containing a polypeptide of the invention,
(b) measuring the amount of labelled ligand bound to the whole cell or the cell membrane;
(c) adding a candidate compound to a mixture of labelled ligand and the whole cell or the cell membrane of step (a) and allowing the mixture to attain equilibrium;
(d) measuring the amount of labelled ligand bound to the whole cell or the cell membrane after step (c); and
(e) comparing the difference in the labelled ligand bound in step (b) and (d), such that the compound which causes the reduction in binding in step (d) is considered to be an agonist or antagonist.

In certain of the embodiments described above, simple binding assays may be used, in which the adherence of a test compound to a surface bearing the polypeptide is detected by means of a label directly or indirectly associated with the test compound or in an assay involving competition with a labelled competitor. In another embodiment, competitive drug screening assays may be used, in which neutralising antibodies that are capable of binding the polypeptide specifically compete with a test compound for binding. In this manner, the antibodies can be used to detect the presence of any test compound that possesses specific binding affinity for the polypeptide.

Alternatively, if the wild type version of the polypeptide of the present invention (INSP058) normally binds to a receptor in nature, then in another aspect of the invention, the polypeptide of the present invention may be an antagonist of the wild type version of the polypeptide. An example of such a polypeptide is thought to be INSP058 SV. In this aspect of the invention, the polypeptide of the present invention is able to compete with the INSP058 polypeptide for the same binding site on the receptor. The INSP058SV polypeptide would not stimulate the receptor, so that the normal biological effect is not induced. The polypeptide of the present invention is therefore a competitive inhibitor of the natural polypeptide. Preferably, a competitive inhibitor according to this aspect of the invention comprises or consists of the amino acid sequence as recited in SEQ ID NO:10 or SEQ ID NO:16. The methods described above for screening antagonists can be readily adapted by a skilled person to screen for competitive inhibitors.

Assays may also be designed to detect the effect of added test compounds on the production of mRNA encoding the polypeptide in cells. For example, an ELISA may be constructed that measures secreted or cell-associated levels of polypeptide using monoclonal or polyclonal antibodies by standard methods known in the art, and this can be used to search for compounds that may inhibit or enhance the production of the polypeptide from suitably manipulated cells or tissues. The formation of binding complexes between the polypeptide and the compound being tested may then be measured.

Assay methods that are also included within the terms of the present invention are those that involve the use of the genes and polypeptides of the invention in overexpression or ablation assays. Such assays involve the manipulation of levels of these genes/polypeptides in cells and assessment of the impact of this manipulation event on the physiology of the manipulated cells. For example, such experiments reveal details of signalling and metabolic pathways in which the particular genes/polypeptides are implicated, generate information regarding the identities of polypeptides with which the studied polypeptides interact and provide clues as to methods by which related genes and proteins are regulated.

Another technique for drug screening which may be used provides for high throughput screening of compounds having suitable binding affinity to the polypeptide of interest (see International patent application WO84/03564). In this method, large numbers of different small test compounds are synthesised on a solid substrate, which may then be reacted with the polypeptide of the invention and washed. One way of immobilising the polypeptide is to use non-neutralising antibodies. Bound polypeptide may then be detected using methods that are well known in the art. Purified polypeptide can also be coated directly onto plates for use in the aforementioned drug screening techniques.

The polypeptide of the invention may be used to identify membrane-bound or soluble receptors, through standard receptor binding techniques that are known in the art, such as ligand binding and crosslinking assays in which the polypeptide is labelled with a radioactive isotope, is chemically modified, or is fused to a peptide sequence that facilitates its detection or purification, and incubated with a source of the putative receptor (for example, a composition of cells, cell membranes, cell supernatants, tissue extracts, or bodily fluids). The efficacy of binding may be measured using biophysical techniques such as surface plasmon resonance (supplied by Biacore AB, Uppsala, Sweden) and spectroscopy. Binding assays may be used for the purification and cloning of the receptor, but may also identify agonists and antagonists of the polypeptide, that compete with the binding of the polypeptide to its receptor. Standard methods for conducting screening assays are well understood in the art.

The invention also includes a screening kit useful in the methods for identifying agonists, antagonists, ligands, receptors, substrates, enzymes, that are described above.

The invention includes the agonists, antagonists, ligands, receptors, substrates and enzymes, and other compounds which modulate the activity or antigenicity of the polypeptide of the invention discovered by the methods that are described above.

The invention also provides pharmaceutical compositions comprising a polypeptide, nucleic acid, ligand or compound of the invention in combination with a suitable pharmaceutical carrier. These compositions may be suitable as therapeutic or diagnostic reagents, as vaccines, or as other immunogenic compositions, as outlined in detail below.

According to the terminology used herein, a composition containing a polypeptide, nucleic acid, ligand or compound [X] is "substantially free of" impurities [herein, Y] when at least 85% by weight of the total X+Y in the composition is X. Preferably, X comprises at least about 90% by weight of the total of X+Y in the composition, more preferably at least about 95%, 98% or even 99% by weight.

The pharmaceutical compositions should preferably comprise a therapeutically effective amount of the polypeptide, nucleic acid molecule, ligand, or compound of the invention.

The term "therapeutically effective amount" as used herein refers to an amount of a therapeutic agent needed to treat, ameliorate, or prevent a targeted disease or condition, or to exhibit a detectable therapeutic or preventative effect. For any compound, the therapeutically effective dose can be estimated initially either in cell culture assays, for example, of neoplastic cells, or in animal models, usually mice, rabbits, dogs, or pigs. The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.01 mg/kg to 50 mg/kg, preferably 0.05 mg/kg to 10 mg/kg. Compositions may be administered individually to a patient or may be administered in combination with other agents, drugs or hormones.

A pharmaceutical composition may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity. Suitable carriers may be large, slowly metabolised macromolecules such as proteins, polysaccharides, polylactic acids, polyglycolic acids, polymeric amino acids, amino acid copolymers and inactive virus particles.

Pharmaceutically acceptable salts can be used therein, for example, mineral acid salts such as hydrochlorides, hydrobromides, phosphates, sulphates, and the like; and the salts of organic acids such as acetates, propionates, malonates, benzoates, and the like. A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The pharmaceutical compositions utilised in this invention may be administered by any number of routes including, but not limited to, oral, intravenous, intramuscular, intra-arterial, intramedullary, intrathecal, intraventricular, transdermal or transcutaneous applications (for example, see WO98/20734), subcutaneous, intraperitoneal, intranasal, enteral, topical, sublingual, intravaginal or rectal means. Gene guns or hyposprays may also be used to administer the pharmaceutical compositions of the invention. Typically, the therapeutic compositions may be prepared as injectables, either as liquid solutions or suspensions; solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

If the activity of the polypeptide of the invention is in excess in a particular disease state, several approaches are available. One approach comprises administering to a subject an inhibitor compound (antagonist) as described above, along with a pharmaceutically acceptable carrier in an amount effective to inhibit the function of the polypeptide, such as by blocking the binding of ligands, substrates, enzymes, receptors, or by inhibiting a second signal, and thereby alleviating the abnormal condition. Preferably, such antagonists are antibodies. Most preferably, such antibodies are chimeric and/or humanised to minimise their immunogenicity, as described previously.

In another approach, soluble forms of the polypeptide that retain binding affinity for the ligand, substrate, enzyme, receptor, in question, may be administered. Typically, the polypeptide may be administered in the form of fragments that retain the relevant portions.

In an alternative approach, expression of the gene encoding the polypeptide can be inhibited using expression blocking techniques, such as the use of antisense nucleic acid molecules (as described above), either internally generated or separately administered. Modifications of gene expression can be obtained by designing complementary sequences or antisense molecules (DNA, RNA, or PNA) to the control, 5' or regulatory regions (signal sequence, promoters, enhancers and introns) of the gene encoding the polypeptide. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al., (1994) In: Huber, B. E. and B. I. Carr, Molecular and Immunologic Approaches, Futura Publishing Co., Mt. Kisco, N.Y.). The complementary sequence or antisense molecule may also be designed to block translation of mRNA by preventing the transcript from binding to ribosomes. Such oligonucleotides may be administered or may be generated in situ from expression in vivo.

In addition, expression of the polypeptide of the invention may be prevented by using ribozymes specific to its encoding mRNA sequence. Ribozymes are catalytically active RNAs that can be natural or synthetic (see for example Usman, N, et al., Curr. Opin. Struct. Biol (1996) 6(4), 527-33). Synthetic ribozymes can be designed to specifically cleave mRNAs at selected positions thereby preventing translation of the mRNAs into functional polypeptide. Ribozymes may be synthesised with a natural ribose phosphate backbone and natural bases, as normally found in RNA molecules. Alternatively the ribozymes may be synthesised with non-natural backbones, for example, 2'-O-methyl RNA, to provide protection from ribonuclease degradation and may contain modified bases.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of non-traditional bases such as inosine, queosine and butosine, as well as acetyl-, methyl-, thio- and similarly modified forms of adenine, cytidine, guanine, thymine and uridine which are not as easily recognised by endogenous endonucleases.

For treating abnormal conditions related to an under-expression of the polypeptide of the invention and its activity, several approaches are also available. One approach comprises administering to a subject a therapeutically effective amount of a compound that activates the polypeptide, i.e., an agonist as described above, to alleviate the abnormal condition. Alternatively, a therapeutic amount of the polypeptide in combination with a suitable pharmaceutical carrier may be administered to restore the relevant physiological balance of polypeptide.

Gene therapy may be employed to effect the endogenous production of the polypeptide by the relevant cells in the subject. Gene therapy is used to treat permanently the inappropriate production of the polypeptide by replacing a defective gene with a corrected therapeutic gene.

Gene therapy of the present invention can occur in vivo or ex vivo. Ex vivo gene therapy requires the isolation and purification of patient cells, the introduction of a therapeutic gene and introduction of the genetically altered cells back into the patient. In contrast, in vivo gene therapy does not require isolation and purification of a patient's cells.

The therapeutic gene is typically "packaged" for administration to a patient. Gene delivery vehicles may be non-viral, such as liposomes, or replication-deficient viruses, such as adenovirus as described by Berkner, K. L., in Curr. Top. Microbiol. Immunol., 158, 39-66 (1992) or adeno-associated virus (AAV) vectors as described by Muzyczka, N., in Curr. Top. Microbiol. Immunol., 158, 97-129 (1992) and U.S. Pat. No. 5,252,479. For example, a nucleic acid molecule encoding a polypeptide of the invention may be engineered for expression in a replication-defective retroviral vector. This expression construct may then be isolated and introduced into a packaging cell transduced with a retroviral plasmid vector containing RNA encoding the polypeptide, such that the packaging cell now produces infectious viral particles containing the gene of interest. These producer cells may be administered to a subject for engineering cells in vivo and expression of the polypeptide in vivo (see Chapter 20, Gene Therapy and other Molecular Genetic-based Therapeutic Approaches, (and references cited therein) in Human Molecular Genetics (1996), T Strachan and A P Read, BIOS Scientific Publishers Ltd).

Another approach is the administration of "naked DNA" in which the therapeutic gene is directly injected into the bloodstream or muscle tissue.

In situations in which the polypeptides or nucleic acid molecules of the invention are disease causing agents, the invention provides that they can be used in vaccines to raise antibodies against the disease-causing agent.

Vaccines according to the invention may either be prophylactic (i.e. to prevent infection) or therapeutic (i.e. to treat disease after infection). Such vaccines comprise immunising antigen(s), immunogen(s), polypeptide(s), protein(s) or nucleic acid, usually in combination with pharmaceutically-acceptable carriers as described above, which include any carrier that does not itself induce the production of antibodies harmful to the individual receiving the composition. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, and other pathogens.

Since polypeptides may be broken down in the stomach, vaccines comprising polypeptides are preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient, and aqueous and non-aqueous sterile suspensions which may include suspending agents or thickening agents.

The vaccine formulations of the invention may be presented in unit-dose or multi-dose containers. For example, sealed ampoules and vials and may be stored in a freeze-dried condition requiring only the addition of the sterile liquid carrier immediately prior to use. The dosage will depend on the specific activity of the vaccine and can be readily determined by routine experimentation.

Genetic delivery of antibodies that bind to polypeptides according to the invention may also be effected, for example, as described in International paten application WO98/55607.

The technology referred to as jet injection (see, for example, see Worldwide Website: powderject.com) may also be useful in the formulation of vaccine compositions.

A number of suitable methods for vaccination and vaccine delivery systems are described in International patent application WO00/29428.

This invention also relates to the use of nucleic acid molecules according to the present invention as diagnostic reagents. Detection of a mutated form of the gene characterised by the nucleic acid molecules of the invention which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acid molecules for diagnosis may be obtained from a subject's cells, such as from blood, urine, saliva, tissue biopsy or autopsy material. The genomic DNA may be used directly for detection or may be amplified enzymatically by using PCR, ligase chain reaction (LCR), strand displacement amplification (SDA), or other amplification techniques (see Saiki et al., Nature, 324, 163-166 (1986); Bej, et al., Crit. Rev. Biochem. Molec. Biol., 26, 301-334 (1991); Birkenmeyer et al., J. Virol. Meth., 35, 117-126 (1991); Van Brunt, J., Bio/Technology, 8, 291-294 (1990)) prior to analysis.

In one embodiment, this aspect of the invention provides a method of diagnosing a disease in a patient, comprising assessing the level of expression of a natural gene encoding a polypeptide according to the invention and comparing said level of expression to a control level, wherein a level that is different to said control level is indicative of disease. The method may comprise the steps of:

a) contacting a sample of tissue from the patient with a nucleic acid probe under stringent conditions that allow the formation of a hybrid complex between a nucleic acid molecule of the invention and the probe;

b) contacting a control sample with said probe under the same conditions used in step a);

c) and detecting the presence of hybrid complexes in said samples;

wherein detection of levels of the hybrid complex in the patient sample that differ from levels of the hybrid complex in the control sample is indicative of disease.

A further aspect of the invention comprises a diagnostic method comprising the steps of:
a) obtaining a tissue sample from a patient being tested for disease;
b) isolating a nucleic acid molecule according to the invention from said tissue sample; and
c) diagnosing the patient for disease by detecting the presence of a mutation in the nucleic acid molecule which is associated with disease.

To aid the detection of nucleic acid molecules in the above-described methods, an amplification step, for example using PCR, may be included.

Deletions and insertions can be detected by a change in the size of the amplified product in comparison to the normal genotype. Point mutations can be identified by hybridizing amplified DNA to labelled RNA of the invention or alternatively, labelled antisense DNA sequences of the invention. Perfectly-matched sequences can be distinguished from mismatched duplexes by RNase digestion or by assessing differences in melting temperatures. The presence or absence of the mutation in the patient may be detected by contacting DNA with a nucleic acid probe that hybridises to the DNA under stringent conditions to form a hybrid double-stranded molecule, the hybrid double-stranded molecule having an unhybridised portion of the nucleic acid probe strand at any portion corresponding to a mutation associated with disease; and detecting the presence or absence of an unhybridised portion of the probe strand as an indication of the presence or absence of a disease-associated mutation in the corresponding portion of the DNA strand.

Such diagnostics are particularly useful for prenatal and even neonatal testing.

Point mutations and other sequence differences between the reference gene and "mutant" genes can be identified by other well-known techniques, such as direct DNA sequencing or single-strand conformational polymorphism, (see Orita et al., Genomics, 5, 874-879 (1989)). For example, a sequencing primer may be used with double-stranded PCR product or a single-stranded template molecule generated by a modified PCR. The sequence determination is performed by conventional procedures with radiolabelled nucleotides or by automatic sequencing procedures with fluorescent-tags. Cloned DNA segments may also be used as probes to detect specific DNA segments. The sensitivity of this method is greatly enhanced when combined with PCR. Further, point mutations and other sequence variations, such as polymorphisms, can be detected as described above, for example, through the use of allele-specific oligonucleotides for PCR amplification of sequences that differ by single nucleotides.

DNA sequence differences may also be detected by alterations in the electrophoretic mobility of DNA fragments in gels, with or without denaturing agents, or by direct DNA sequencing (for example, Myers et al., Science (1985) 230: 1242). Sequence changes at specific locations may also be revealed by nuclease protection assays, such as RNase and S1 protection or the chemical cleavage method (see Cotton et al., Proc. Natl. Acad. Sci. USA (1985) 85: 4397-4401).

In addition to conventional gel electrophoresis and DNA sequencing, mutations such as microdeletions, aneuploidies, translocations, inversions, can also be detected by in situ analysis (see, for example, Keller et al., DNA Probes, 2nd Ed., Stockton Press, New York, N.Y., USA (1993)), that is, DNA or RNA sequences in cells can be analysed for mutations without need for their isolation and/or immobilisation onto a membrane. Fluorescence in situ hybridization (FISH) is presently the most commonly applied method and numerous reviews of FISH have appeared (see, for example, Trachuck et al, Science, 250, 559-562 (1990), and Trask et al., Trends, Genet., 7, 149-154 (1991)).

In another embodiment of the invention, an array of oligonucleotide probes comprising a nucleic acid molecule according to the invention can be constructed to conduct efficient screening of genetic variants, mutations and polymorphisms. Array technology methods are well known and have general applicability and can be used to address a variety of questions in molecular genetics including gene expression, genetic linkage, and genetic variability (see for example: M. Chee et al., Science (1996), Vol 274, pp 610-613).

In one embodiment, the array is prepared and used according to the methods described in PCT application WO95/11995 (Chee et al.); Lockhart, D. J. et al., (1996) Nat. Biotech. 14: 1675-1680; and Schena, M. et al, (1996) Proc. Natl. Acad. Sci. 93:10614-10619). Oligonucleotide pairs may range from two to over one million. The oligomers are synthesized at designated areas on a substrate using a light-directed chemical process. The substrate may be paper, nylon or other type of membrane, filter, chip, glass slide or any other suitable solid support. In another aspect, an oligonucleotide may be synthesized on the surface of the substrate by using a chemical coupling procedure and an ink jet application apparatus, as described in PCT application WO95/25116 (Baldeschweiler et al.). In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and over one million which lends itself to the efficient use of commercially-available instrumentation.

In addition to the methods discussed above, diseases may be diagnosed by methods comprising determining, from a sample derived from a subject, an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods.

Assay techniques that can be used to determine levels of a polypeptide of the present invention in a sample derived from a host are well-known to those of skill in the art and are discussed in some detail above (including radioimmunoassays, competitive-binding assays, Western Blot analysis and ELISA assays). This aspect of the invention provides a diagnostic method which comprises the steps of: (a) contacting a ligand as described above with a biological sample under conditions suitable for the formation of a ligand-polypeptide complex; and (b) detecting said complex.

Protocols such as ELISA (as previously described), RIA, and FACS for measuring polypeptide levels may additionally provide a basis for diagnosing altered or abnormal levels of polypeptide expression. Normal or standard values for polypeptide expression are established by combining body fluids or cell extracts taken from normal mammalian subjects, preferably humans, with antibody to the polypeptide under conditions suitable for complex formation. The amount of standard complex formation may be quantified by various methods, such as by photometric means.

Antibodies which specifically bind to a polypeptide of the invention may be used for the diagnosis of conditions or diseases characterised by expression of the polypeptide, or in assays to monitor patients being treated with the polypeptides, nucleic acid molecules, ligands and other compounds of the invention. Antibodies useful for diagnostic purposes may be prepared in the same manner as those described above for therapeutics. Diagnostic assays for the polypeptide include methods that utilise the antibody and a label to detect the polypeptide in human body fluids or extracts of cells or tissues. The antibodies may be used with or without modification, and may be labelled by joining them, either covalently or non-covalently, with a reporter molecule. A wide variety of reporter molecules known in the art may be used, several of which are described above.

Quantities of polypeptide expressed in subject, control and disease samples from biopsied tissues are compared with the standard values. Deviation between standard and subject values establishes the parameters for diagnosing disease. Diagnostic assays may be used to distinguish between absence, presence, and excess expression of polypeptide and to monitor regulation of polypeptide levels during therapeutic intervention. Such assays may also be used to evaluate the efficacy of a particular therapeutic treatment regimen in animal studies, in clinical trials or in monitoring the treatment of an individual patient.

A diagnostic kit of the present invention may comprise:
(a) a nucleic acid molecule of the present invention;
(b) a polypeptide of the present invention; or
(c) a ligand of the present invention.

In one aspect of the invention, a diagnostic kit may comprise a first container containing a nucleic acid probe that hybridises under stringent conditions with a nucleic acid molecule according to the invention; a second container containing primers useful for amplifying the nucleic acid molecule; and instructions for using the probe and primers for facilitating the diagnosis of disease. The kit may further comprise a third container holding an agent for digesting unhybridised RNA.

In an alternative aspect of the invention, a diagnostic kit may comprise an array of nucleic acid molecules, at least one of which may be a nucleic acid molecule according to the invention.

To detect polypeptide according to the invention, a diagnostic kit may comprise one or more antibodies that bind to a polypeptide according to the invention; and a reagent useful for the detection of a binding reaction between the antibody and the polypeptide.

Such kits will be of use in diagnosing a disease or susceptibility to disease, such as cell proliferative disorders, including neoplasm, melanoma, lung, colorectal, breast, pancreas, head and neck and other solid tumours; myeloproliferative disorders, such as leukemia, non-Hodgkin lymphoma, leukopenia, thrombocytopenia, angiogenesis disorder, Kaposi' sarcoma; autoimmune/inflammatory disorders, including allergy, inflammatory bowel disease, arthritis, psoriasis and respiratory tract inflammation, asthma, and organ transplant rejection; cardiovascular disorders, including hypertension, oedema, angina, atherosclerosis, thrombosis, sepsis, shock, reperfusion injury, and ischemia; neurological disorders including central nervous system disease, Alzheimer's disease, brain injury, amyotrophic lateral sclerosis, and pain; developmental disorders; metabolic disorders including diabetes mellitus, osteoporosis, and obesity, AIDS and renal disease; infections including viral infection, bacterial infection, fungal infection and parasitic infection; and other disorders mediated by TNF-like secreted proteins, particularly those mediated by C1q family proteins.

Various aspects and embodiments of the present invention will now be described in more detail by way of example, with particular reference to the INSP058 polypeptide. It will be appreciated that modification of detail may be made without departing from the scope of the invention.

BRIEF DESCRIPTION OF THE FIGURES

FIG. 1: Top ten results from BLAST against the NCBI non-redundant database using SEQ ID NO:8 (INSP058 polypeptide sequence).

FIG. 2: Alignment generated by BLAST between SEQ ID NO:8 (INSP058 polypeptide sequence) and the closest related sequence, otolin-1 from *Oncorhynchus keta*.

FIG. 3: Top 20 results from Genome Threader using SEQ ID NO:8 (INSP058 polypeptide sequence). The PDB codes for the top three results refer to the following protein structures: 1c28 chains A, C and B. The crystal structure of a complement-1q family protein suggests an evolutionary link to tumor necrosis factor.

FIG. 4: Structural alignment generated by Genome Threader between SEQ ID NO:8 (INSP058 polypeptide sequence) and the top PDB structure in FIG. 3 (1c28).

FIG. 6: Predicted nucleotide sequence of INSP058 with translation (SEQ ID NO:27 and SEQ ID NO:8).

FIG. 7: Nucleotide sequence with translation of PCR product cloned using primers INSP058-CP1 and INSP058-CP2 (SEQ ID Nos:28-33).

FIG. 8: Map of pCRII-TOPO-INSP058SV.

FIG. 9: Alignment of cloned nucleotide sequence of INSP058 (INSP058SV, SEQ ID NO:34)) with predicted INSP058 sequence (SEQ ID NO:27).

FIG. 10: Alignment of INSP058 predicted amino acid sequence (SEQ ID NO:8) with amino acid sequence of cloned INSP058SV (SEQ ID NO:35).

FIG. 11: Map of expression vector pEAK12d.

FIG. 12: Map of Gateway vector pDONR201.

FIG. 13: Map of pEAK12d-INSP058 SV-6HIS.

EXAMPLES

Example 1

INSP058

SEQ ID NO:8 was used as a BLAST query against the NCBI non-redundant Sequence database. The closest match to the query sequence is for otolin-1 from *Oncorliynchus keta* (FIG. 1). FIG. 2 shows the alignment of the INSP058 query sequence to the sequence of otolin-1 from *Oncorynchus keta*. FIG. 3 shows the top 20 results from Genome Threader using SEQ ID NO:8 (INSP058 polypeptide sequence). The PDB codes for the top three results refer to the following protein structures: 1c28 chains A, C and B. The crystal structure of a complement-1q family protein suggests an evolutionary link to tumor necrosis factor. FIG. 4 shows the structural alignment generated by Genome Threader between SEQ ID NO:8 (INSP058 polypeptide sequence) and the top PDB structure in FIG. 3 (1c28).

Figure 5A:
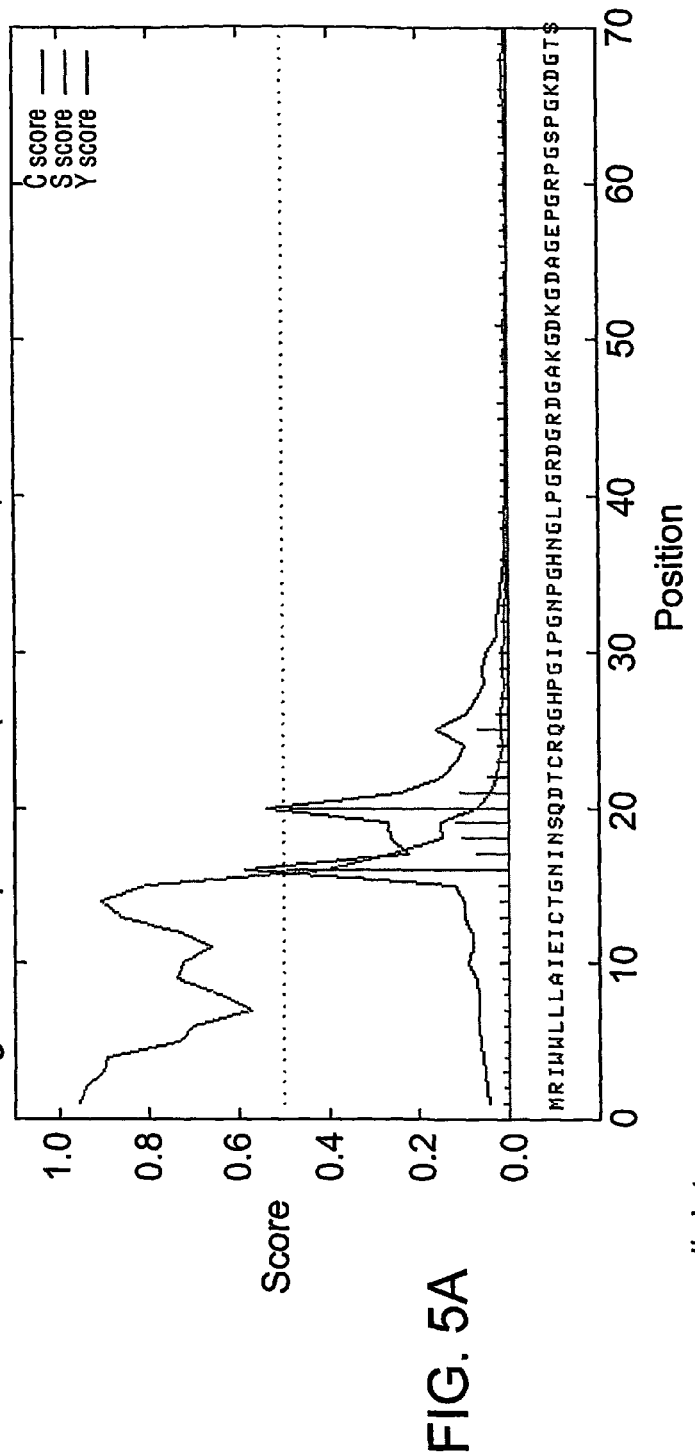
FIG. 5A: SignalP-NN prediction of the signal peptide present in the INSP058 polypeptide sequence (SEQ ID NO:8).
Figure 5B:
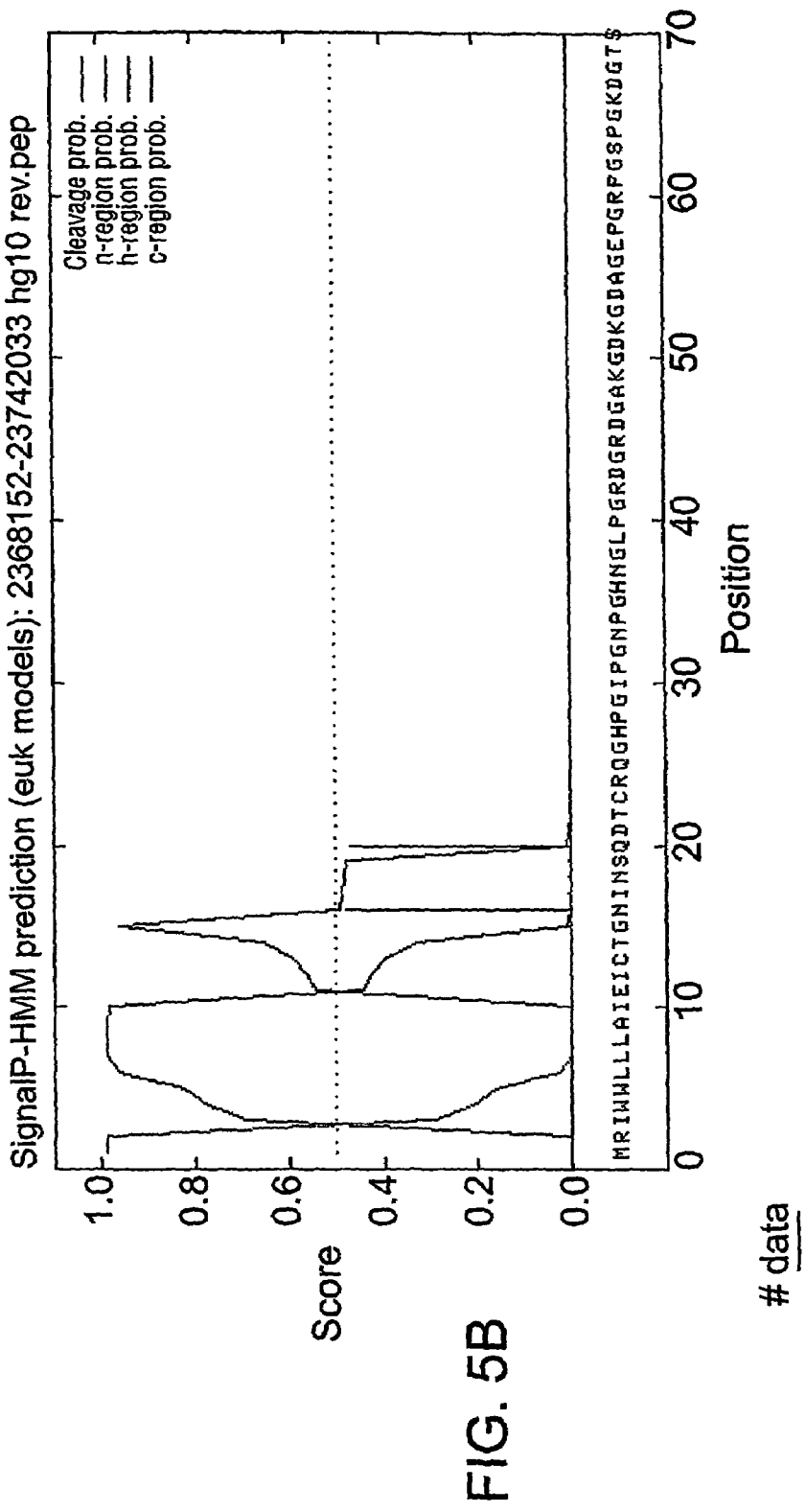
FIG. 5B: SignalP-HMM prediction of the signal peptide present in the INSP058 polypeptide sequence (SEQ ID NO:8).

The INSP058 polypeptide sequence (SEQ ID NO:8) was subjected to analysis using SignalP v2.0 see Worldwide Website: cbs.dtu.dk/services/SignalP-2.0), a program that predicts the presence and location of signal peptide cleavage sites in amino acid sequences from different organisms. SignalP v2.0 comprises two signal peptide prediction methods, SignalP-NN (based on neural networks) and SignalP-HMM (based on hidden Markov models). The SignalP results for INSP058 polypeptide sequence (SEQ ID NO:8) are shown as FIGS. 5A and 5B. FIGS. 5A and 5B show that the most likely cleavage site for INSP058 polypeptide sequence (SEQ ID NO:8) falls between positions 15 and 16.

Example 2

INSP058 Splice Variant 1.1 cDNA Libraries

Human cDNA libraries (in bacteriophage lambda (λ) vectors) were purchased from Stratagene or Clontech or prepared at the Serono Pharmaceutical Research Institute in λ ZAP or λ GT10 vectors according to the manufacturer's protocol (Stratagene). Bacteriophage λ DNA was prepared from small scale cultures of infected *E. coli* host strain using the Wizard Lambda Preps DNA purification system according to the manufacturer's instructions (Promega, Corporation, Madison Wis.) The list of libraries and host strains used is shown in Table 1. Seven pools representing 26 different libraries (100 ng/μl phage DNA) or phage DNA from individual libraries were used in subsequent PCR reactions.

1.2 PCR of Virtual cDNAs from Phage Library DNA

Gene-specific PCR amplification primers (INSP058-CP1 and INSP058-CP2, FIG. 6 and Table 2) were designed to amplify a 990 bp product expected to contain almost the full predicted coding sequence of INSP058. These were used in PCR on the phage cDNA library pools shown in Table 1. The PCR was performed in a final volume of 50 μl containing 1× AmpliTaq™ buffer, 200 μM dNTPs, 50 pmoles each of cloning primers, 2.5 units of AmpliTaq™ (Perkin Elmer) and 100 ng of each phage library pool DNA using an MJ Research DNA Engine, programmed as follows: 40 cycles at 94° C. for 1 min and 72° C. for 1 min; followed by 1 cycle at 72° C. for 7 min and a holding cycle at 4° C.

TABLE 2

INSP058 cloning and sequencing primers

| Primer | Sequence (5'-3') |
| --- | --- |
| INSP058-GP1 | CTG GTG GCT TCT GCT TGC CAT T (SEQ ID:17) |
| INSP058-CP2 | GGG GCT GCT GAA CAG AAG GAA C (SEQ ID:18) |
| GCP Forward | G GGG ACA AGT TTG TAC AAA AAA GCA GGC TTC GCC ACC (SEQ ID:19) |
| GCP Reverse | GGG GAC CAC TTT GTA CAA GAA AGC TGG GTT TCA *ATG GTG ATG GTG ATG GTG* (SEQ ID:20) |
| INSP058SV-EX1 | GCA GGC TTC GCC ACC ATG AGG ATC TGG TGG CTT CTG CTT GCC ATT (SEQ ID:21) |
| INSP058SV-EX2 | *GTG ATG GTG ATG GTG* CTC CGT TTT TGA CCA AAG ACA CCT GAA CA (SEQ ID:22) |

TABLE 1

Human cDNA libraries

| Library | Tissue/cell source | Vector | Host strain | Supplier | Cat. no. |
| --- | --- | --- | --- | --- | --- |
| 6 | human substantia nigra | GT10 | LE392 | in house | |
| 7 | human fetal brain | GT10 | LE392 | in house | |
| 8 | human cortex brain | GT10 | LE392 | in house | |
| 9 | human colon | GT10 | LE392 | Clontech | HL1034a |
| 11 | human fetal lung | GT10 | LE392 | Clontech | HL1072a |
| 12 | human fetal kidney | GT10 | LE392 | Clontech | HL1071a |
| 14 | human bone marrow | GT10 | LE392 | Clontech | HL1058a |
| 18 | human U373 cell line | GT10 | LE392 | in house | |
| 19 | human CFPoc-1 cell line | Uni Zap | XL1-Blue MRF' | Stratagene | 936206 |
| 20 | human retina | GT10 | LE392 | Clontech | HL1132a |
| 21 | human urinary bladder | GT10 | LE392 | in house | |
| 22 | human platelets | Uni Zap | XL1-Blue MRF' | in house | |
| 23 | human neuroblastoma Kan + TS | GT10 | LE392 | in house | |
| 24 | human bronchial smooth muscle | GT10 | LE392 | in house | |
| 25 | human bronchial smooth muscle | GT10 | LE392 | in house | |
| 26 | human Thymus | GT10 | LE392 | Clontech | HL1127a |
| 27 | human spleen 5' stretch | GT11 | LE392 | Clontech | HL1134b |
| 28 | human peripheral blood monocytes | GT10 | LE392 | Clontech | HL1050a |
| 29 | human testis | GT10 | LE392 | Clontech | HL1065a |
| 30 | human fetal brain | GT10 | LE392 | Clontech | HL1065a |
| 31 | human substantia nigra | GT10 | LE392 | Clontech | HL1093a |
| 32 | human placenta #11 | GT11 | LE392 | Clontech | HL1075b |
| 33 | human Fetal brain | GT10 | LE392 | Clontech | custom |
| 34 | human placenta #59 | GT10 | LE392 | Clontech | HL5014a |
| 35 | human pituitary | GT10 | LE392 | Clontech | HL1097a |
| 36 | human pancreas #63 | Uni Zap XR | XL1-Blue MRF' | Stratagene | 937208 |

TABLE 2-continued

INSP058 cloning and sequencing primers

| Primer | Sequence (5'-3') |
|---|---|
| pEAK12-F | GCC AGC TTG GCA CTT GAT GT (SEQ ID:23) |
| pEAK12-R | GAT GGA GGT GGA CGT GTC AG (SEQ ID:24) |
| SP6 | ATT TAG GTG ACA CTA TAG (SEQ ID:25) |
| T7 | TAA TAC GAC TCA CTA TAG GG (SEQ ID:26) |

Underlined sequence = Kozak sequence; Bold = Stop codon and *Italic* sequence = HIS tag The amplification products were visualized on 0.8% agarose gels in 1× TAE buffer (Invitrogen) and were purified from the gel using the Wizard PCR Preps DNA Purification System (Promega). PCR products eluted in 50 µl of sterile water were either subcloned directly or stored at −20 C. −20° C.

1.3 Gene Specific Cloning Primers for PCR

A pair of PCR primers having a length of between 18 and 25 bases were designed for amplifying a partial sequence of INSP058 cDNA using Primer Designer Software (Scientific & Educational Software, PO Box 72045, Durham, N.C. 27722-2045, USA). PCR primers were optimized to have a Tm close to 55+10° C. and a GC content of 40-60%. Primers were selected which had high selectivity for the target sequence INSP058 (little or no none specific priming). INSP058-CP1 lacks the first 8 bp of the INSP058 predicted coding sequence due to optimization of the PCR primer design.

1.4 Subcloning of PCR Products

PCR products were subcloned into the topoisomerase I modified cloning vector (pCRII TOPO) using the TA cloning kit purchased from the Invitrogen Corporation using the conditions specified by the manufacturer. Briefly, 4 µl of gel purified PCR product from the human library pool P amplification was incubated for 15 min at room temperature with 1 µl of TOPO vector and 1 µl salt solution. The reaction mixture was then transformed into *E. coli* strain TOP10 (Invitrogen) as follows: a 50 µl aliquot of One Shot TOP10 cells was thawed on ice and 2 µl of TOPO reaction was added. The mixture was incubated for 15 min on ice and then heat shocked by incubation at 42° C. for exactly 30 s. Samples were returned to ice and 250 µl of warm SOC media (room temperature) was added. Samples were incubated with shaking (220 rpm) for 1 h at 37° C. The transformation mixture was then plated on L-broth (LB) plates containing ampicillin (100 µg/ml) and incubated overnight at 37° C.

1.5 Selection of Amplicillin Resistant Colonies

A number of ampicillin resistant colonies were selected and the cells stabbed into individual wells of a 96 well plate each containing L-broth containing ampicillin (100 µg/ml).

1.6 Plasmid DNA Preparation and Sequencing

Miniprep plasmid DNA was prepared from the stab cultures and subjected to DNA sequencing with T7 primer at GATC Biotech AG (Jakob-Stadler-Platz 7, D-78467 Konstanz). The sequence of the cloned cDNA fragment is shown in FIG. 7.

2. Identification of cDNA Libraries/Templates Containing INSP058 SV

PCR products obtained with INSP058-CP1 and INSP058-CP2 and migrating at 453 bp, a smaller size than expected, were identified in λ cDNA library Pool P (human thymus, spleen, peripherial blood monocytes, and testis). The plasmid map of the cloned PCR product (pCRII-TOPO-INSP058) (plasmid ID number 12917) is shown in FIG. 8. The cloned sequence lacks the first 8 bp of the INSP058 predicted coding sequence but is otherwise identical to the predicted INSP058 sequence up to nucleotide position 267 where it diverges from the prediction due to a 538 bp deletion (FIG. 9). Translation of the longest ORF (including the 8 bp missing at the 5' end) yields a protein of 99 amino acids of which amino acids 1-89 are identical to the INSP058 prediction (FIG. 11). The cloned sequence therefore corresponds to a short splice variant of INSP058 (called INSP058 SV).

3. Construction of Plasmids for Expression of INSP058SV in HEK293/EBNA Cells.

A pCRII-TOPO clone containing the coding sequence (ORF) of INSP058SV identified by DNA sequencing (FIG. 7) was then used to subclone the insert into the mammalian cell expression vector pEAK12d (FIG. 11) using the Gateway™ cloning methodology (Invitrogen).

3.1 Generation of Gateway Compatible INSP058SV ORF Fused to an in Frame 6HIS Tag Sequence The first stage of the Gateway cloning process involves a two step PCR reaction which generates the ORF of INSP058SV flanked at the 5' end by an attB1 recombination site and Kozak sequence, and flanked at the 3' end by a sequence encoding an in frame 6 histidine (6HIS) tag, a stop codon and the attB2 recombination site (Gateway compatible cDNA). The first PCR reaction (in a final volume of 50 µl) contains: 1.5 µl (approx. 25 ng) of pCR II TOPO-INSP058SV (plasmid 12917 and FIG. 8), 1.5 µl dNTPs (10 mM), 5 µl of 10× Pfx polymerase buffer, 1 µl MgSO4 (50 mM), 0.5 µl each of gene specific primer (100 µM) (INSP058-EX1 forward and INSP058-EX2 reverse) and 0.5 µl Platinum Pfx DNA polymerase (Invitrogen). The PCR reaction was performed using an initial denaturing step of 95° C. for 1 min, followed by 10 cycles of 94° C. for 15 s; 55° C. for 30 s and 68° C. for 2 min; and a holding cycle of 4° C. PCR products were purified directly from the reaction mixture using the Wizard PCR prep DNA purification system (Promega) according to the manufacturer's instructions. The second PCR reaction (in a final volume of 50 µl) contained 10 µl purified PCR product, 1.5 µl dNTPs (10 mM), 5 µl of 10× Pfx polymerase buffer, 1 µl MgSO4 (50 mM), 0.5 µl of each Gateway conversion primer (100 µM) (GCP forward and GCP reverse) and 0.5 µl of Platinum Pfx DNA polymerase. The conditions for the 2nd PCR reaction were: 95° C. for 1 min; 4 cycles of 94° C., 15 sec; 50° C., 30 sec and 68° C. for 2 min; 25 cycles of 94° C., 15 sec; 55° C., 30 sec and 68° C., 2 min; followed by a holding cycle of 4° C. PCR products were purified as described above.

3.2 Subcloning of Gateway Compatible INSP058SV ORF into Gateway Entry Vector pDONR201 and Expression Vector pEAK12d The second stage of the Gateway cloning process involves subcloning of the Gateway modified PCR product into the Gateway entry vector pDONR201 (Invitrogen, FIG. 12) as follows: 5 µl of purified PCR product is incubated with 1.5 µl pDONR201 vector (0.1 µg/µl), 2 µl BP buffer and 1.5 µl of BP clonase enzyme mix (Invitrogen) at RT for 1 h. The reaction was stopped by addition of proteinase K (2 µg) and incubated at 37° C. for a further 10 min. An aliquot of this reaction (2 µl)

was transformed into *E. coli* DH10B cells by electroporation using a Biorad Gene Pulser. Transformants were plated on LB-kanamycin plates. Plasmid mini-prep DNA was prepared from 1-4 of the resultant colonies using Wizard Plus SV Minipreps kit (Promega), and 1.5 µl of the plasmid eluate was then used in a recombination reaction containing 1.5 µl pEAK12d vector (FIG. 9) (0.1 µg/µl), 2 µl LR buffer and 1.5 µl of LR clonase (Invitrogen) in a final volume of 10 µl. The mixture was incubated at RT for 1 h, stopped by addition of proteinase K (2 µg) and incubated at 37° C. for a further 10 min. An aliquot of this reaction (1 µl) was used to transform *E. coli* DH10B cells by electroporation.

Clones containing the correct insert were identified by performing colony PCR as described above except that pEAK12d primers (pEAK12d F and pEAK12d R) were used for the PCR. Plasmid mini prep DNA was isolated from clones containing the correct insert using a Qiaprep Turbo 9600 robotic system (Qiagen) or manually using a Wizard Plus SV minipreps kit (Promega) and sequence verified using the pEAK12d F and pEAK12d R primers.

CsCl gradient purified maxi-prep DNA of plasmid pEAK12d-INSP058 SV-6HIS (plasmid ID number 13081, FIG. 13) was prepared from a 500 ml culture of sequence verified clones (Sambrook J. et al., in Molecular Cloning, a Laboratory Manual, 2nd edition, 1989, Cold Spring Harbor Laboratory Press), resuspended at a concentration of 1 µg/µl in sterile water and stored at −20 C.

In addition, further experiments may now be performed using the pEAK12d-INSP058 SV-6HIS expression vector. Transfection of mammalian cell lines with this vector may enable the high level expression of the INSP058SV protein and thus enable the continued investigation of the functional characteristics of the INSP058SV polypeptides. The following material and methods are an example of those suitable in such experiments:

Cell Culture

Human Embryonic Kidney 293 cells expressing the Epstein-Barr virus Nuclear Antigen (HEK293-EBNA, Invitrogen) are maintained in suspension in Ex-cell VPRO serum-free medium (seed stock, maintenance medium, JRH). Sixteen to 20 hours prior to transfection (Day-1), cells are seeded in 2× T225 flasks (50 ml per flask in DMEM/F12 (1:1) containing 2% FBS seeding medium (JRH) at a density of 2×10$^5$ cells/ml). The next day (transfection day 0) transfection takes place using the JetPEI™ reagent (2 µl/µg of plasmid DNA, PolyPlus-transfection). For each flask, plasmid DNA is co-transfected with GFP (fluorescent reporter gene) DNA. The transfection mix is then added to the 2×T225 flasks and incubated at 37° C. (5% CO$_2$) for 6 days. Confirmation of positive transfection may be carried out by qualitative fluorescence examination at day 1 and day 6 (Axiovert 10 Zeiss).

On day 6 (harvest day), supernatants from the two flasks are pooled and centrifuged (e.g. 4° C., 400 g) and placed into a pot bearing a unique identifier. One aliquot (500 µl) is kept for QC of the 6His-tagged protein (internal bioprocessing QC).

Scale-up batches may be produced by following the protocol called "PEI transfection of suspension cells", referenced BP/PEI/HH/02/04, with PolyEthyleneImine from Polysciences as transfection agent.

Purification Process

The culture medium sample containing the recombinant protein with a C-terminal 6His tag is diluted with cold buffer A (50 mM NaH$_2$PO$_4$; 600 mM NaCl; 8.7% (w/v) glycerol, pH 7.5). The sample is filtered then through a sterile filter (Millipore) and kept at 4° C. in a sterile square media bottle (Nalgene).

The purification is performed at 4° C. on the VISION workstation (Applied Biosystems) connected to an automatic sample loader (Labomatic). The purification procedure is composed of two sequential steps, metal affinity chromatography on a Poros 20 MC (Applied Biosystems) column charged with Ni ions (4.6×50 mm, 0.83 ml), followed by gel filtration on a Sephadex G-25 medium (Amersham Pharmacia) column (1,0×10 cm).

For the first chromatography step the metal affinity column is regenerated with 30 column volumes of EDTA solution (100 mM EDTA; 1 M NaCl; pH 8.0), recharged with Ni ions through washing with 15 column volumes of a 100 mM NiSO$_4$ solution, washed with 10 column volumes of buffer A, followed by 7 column volumes of buffer B (50 mM NaH$_2$PO$_4$; 600 mM NaCl; 8.7% (w/v) glycerol, 400 mM; imidazole, pH 7.5), and finally equilibrated with 15 column volumes of buffer A containing 15 mM imidazole. The sample is transferred, by the Labomatic sample loader, into a 200 ml sample loop and subsequently charged onto the Ni metal affinity column at a flow rate of 10 ml/min. The column is washed with 12 column volumes of buffer A, followed by 28 column volumes of buffer A containing 20 mM imidazole. During the 20 mM imidazole wash loosely attached contaminating proteins are eluted from the column. The recombinant His-tagged protein is finally eluted with 10 column volumes of buffer B at a flow rate of 2 ml/min, and the eluted protein is collected.

For the second chromatography step, the Sephadex G-25 gel-filtration column is regenerated with 2 ml of buffer D (1.137 M NaCl; 2.7 mM KCl; 1.5 mM KH$_2$PO$_4$; 8 mM Na$_2$HPO$_4$; pH 7.2), and subsequently equilibrated with 4 column volumes of buffer C (137 mM NaCl; 2.7 mM KCl; 1.5 mM KH$_2$PO$_4$; 8 mM Na$_2$HPO$_4$; 20% (w/v) glycerol; pH 7.4). The peak fraction eluted from the Ni-column is automatically loaded onto the Sephadex G-25 column through the integrated sample loader on the VISION and the protein is eluted with buffer C at a flow rate of 2 ml/min. The fraction was filtered through a sterile centrifugation filter (Millipore), frozen and stored at −80° C. An aliquot of the sample is analyzed on SDS-PAGE (4-12% NuPAGE gel; Novex) Western blot with anti-His antibodies. The NuPAGE gel may be stained in a 0.1% coomassie blue R250 staining solution (30% methanol, 10% acetic acid) at room temperature for 1 h and subsequently destained in 20% methanol, 7.5% acetic acid until the background is clear and the protein bands clearly visible.

Following the electrophoresis the proteins are electrotransferred from the gel to a nitrocellulose membrane. The membrane is blocked with 5% milk powder in buffer E (137 mM NaCl; 2.7 mM KCl; 1.5 mM KH$_2$PO$_4$; 8 mM Na$_2$HPO$_4$; 0.1% Tween 20, pH 7.4) for 1 h at room temperature, and subsequently incubated with a mixture of 2 rabbit polyclonal anti-His antibodies (G-18 and H-15, 0.2 ug/ml each; Santa Cruz) in 2.5% milk powder in buffer E overnight at 4° C. After a further 1 hour incubation at room temperature, the membrane is washed with buffer E (3×10 min), and then incubated with a secondary HRP-conjugated anti-rabbit antibody (DAKO, HRP 0399) diluted 1/3000 in buffer E containing 2.5% milk powder for 2 hours at room temperature. After washing with buffer E (3×10 minutes), the membrane is developed with the ECL kit (Amersham Pharmacia) for 1 min. The membrane is subsequently exposed to a Hyperfilm (Amersham Pharmacia), the film developed and the western blot image visually analysed.

For samples that showed detectable protein bands by Coomassie staining, the protein concentration may be determined using the BCA protein assay kit (Pierce) with bovine serum albumin as standard.

Furthermore, overexpression or knock-down of the expression of INSP058 SV polypeptides in cell lines may be used to determine the effect on transcriptional activation of the host cell genome. Dimerisation partners, co-activators and co-repressors of the INSP058SV polypeptides may be identified by immunoprecipitation combined with Western blotting and immunoprecipitation combined with mass spectroscopy.

We claim:

1. An isolated polypeptide selected from the group consisting of:
   a) an isolated polypeptide consisting of SEQ ID NO: 10, SEQ ID NO: 14 or SEQ ID NO: 16; and
   b) an isolated polypeptide comprising SEQ ID NO: 10 or SEQ ID NO:16.

2. The isolated polypeptide of claim 1, wherein said polypeptide consists of SEQ ID NO: 10.

3. The isolated polypeptide of claim 1, wherein said polypeptide consists of SEQ ID NO: 14.

4. The isolated polypeptide of claim 1, wherein said polypeptide consists of SEQ ID NO: 16.

5. The isolated polypeptide of claim 1, wherein said polypeptide comprises SEQ ID NO: 10.

6. The isolated polypeptide of claim 1, wherein said polypeptide comprises SEQ ID NO: 16.

* * * * *

UNITED STATES PATENT AND TRADEMARK OFFICE
CERTIFICATE OF CORRECTION

PATENT NO. : 7,514,533 B2  
APPLICATION NO. : 10/557400  
DATED : April 7, 2009  
INVENTOR(S) : Stephen Noel Fitzgerald et al.

It is certified that error appears in the above-identified patent and that said Letters Patent is hereby corrected as shown below:

Column 9,  
Line 22, "INSP058 SV" should read --INSP058SV--.

Column 12,  
Line 62, "examiined" should read --examined--.

Column 15,  
Line 3, "data Such" should read --data. Such--.

Column 17,  
Line 47, "kidney (B3HK)" should read --kidney (BHK)--.

Column 21,  
Line 51, "INSP058 SV" should read --INSP058SV--.

Column 30,  
Line 49, "Map of pEAK12d-INSP058 SV-6HIS" should read  
    --Map of pEAK12d-INSP058SV-6HIS--.  
Line 59, "*Oncorliynchus keta*" should read --*Oncorhynchus keta*--.

Column 32,  
Table 2, line 19, "INSP058-GP1" should read --INSP058-CP1--.

Column 34,  
Line 2, "INSP058 SV" should read --INSP058SV--.  
Line 17, "INSP058 SV" should read --INSP058SV--.

UNITED STATES PATENT AND TRADEMARK OFFICE
CERTIFICATE OF CORRECTION

PATENT NO. : 7,514,533 B2
APPLICATION NO. : 10/557400
DATED : April 7, 2009
INVENTOR(S) : Stephen Noel Fitzgerald et al.

It is certified that error appears in the above-identified patent and that said Letters Patent is hereby corrected as shown below:

Column 35,
Line 22, "pEAK12d-INSP058 SV-6HIS" should read --pEAK12d-INSP058SV-6HIS--.
Line 30, "pEAK12d-INSP058 SV-6HIS" should read --pEAK12d-INSP058SV-6HIS--.

Column 37,
Line 6, "INSP058 SV" should read --INSP058SV--.

Signed and Sealed this

Twenty-third Day of June, 2009

JOHN DOLL
*Acting Director of the United States Patent and Trademark Office*

SEQUENCE LISTING

<160> NUMBER OF SEQ ID NOS: 26

<210> SEQ ID NO 1
<211> LENGTH: 166
<212> TYPE: DNA
<213> ORGANISM: Homo sapiens

<400> SEQUENCE: 1

```
atgaggatct ggtggcttct gcttgccatt gaaatctgca cagggaacat aaactcacag      60
gacacctgca ggcaagggca ccctggaatc cctgggaacc ccggtcacaa tggtctgcct     120
ggaagagatg gacgagacgg agcgaagggt gacaaaggcg atgcag                    166
```

<210> SEQ ID NO 2
<211> LENGTH: 56
<212> TYPE: PRT
<213> ORGANISM: Homo sapiens

<400> SEQUENCE: 2

```
Met Arg Ile Trp Trp Leu Leu Leu Ala Ile Glu Ile Cys Thr Gly Asn
1               5                   10                  15

Ile Asn Ser Gln Asp Thr Cys Arg Gln Gly His Pro Gly Ile Pro Gly
            20                  25                  30

Asn Pro Gly His Asn Gly Leu Pro Gly Arg Asp Gly Arg Asp Gly Ala
        35                  40                  45

Lys Gly Asp Lys Gly Asp Ala Gly
    50                  55
```

<210> SEQ ID NO 3
<211> LENGTH: 63
<212> TYPE: DNA
<213> ORGANISM: Homo sapiens

<400> SEQUENCE: 3

```
gagaaccagg acgtcctggc agcccgggga aggatgggac gagtggagag aagggagaac      60
gag                                                                    63
```

<210> SEQ ID NO 4
<211> LENGTH: 21
<212> TYPE: PRT
<213> ORGANISM: Homo sapiens

<400> SEQUENCE: 4

```
Glu Pro Gly Arg Pro Gly Ser Pro Gly Lys Asp Gly Thr Ser Gly Glu
1               5                   10                  15

Lys Gly Glu Arg Gly
            20
```

<210> SEQ ID NO 5
<211> LENGTH: 770
<212> TYPE: DNA
<213> ORGANISM: Homo sapiens

<400> SEQUENCE: 5

```
gagcagatgg aaaagttgaa gcaaaaggca tcaaaggtga tcaaggctca agaggatccc      60
caggaaaaca tggccccaag gggcttgcag ggcccatggg agagaagggc ctccgaggag     120
agactgggcc tcaggggcag aaggggaata agggtgacgt gggtcccact ggtcctgagg     180
ggccaagggg caacattggg cctttgggcc caactggttt accgggcccc atgggcccta     240
ttggaaagcc tggtcccaaa ggagaagctg gacccacggg gccccagggt gagccaggag     300
tccggggaat aagaggctgg aaaggagatc gaggagagaa agggaaaatc ggtgagactc     360
tagtcttgcc aaaaagtgct ttcactgtgg ggctcacggt gctgagcaag tttccttctt     420
cagatatgcc cattaaattt gataagatcc tgtataacga attcaaccat tatgatacag     480
cagcggggaa attcacgtgc cacattgctg gggtctatta cttcacctac acatcactg      540 ttttctccag aaatgttcag gtgtctttgg tcaaaaatgg agtaaaaata ctgcacacca     600
aagatgctta catgagctct gaggaccagg cctctggcgg cattgtcctg cagctgaagc     660
tcggggatga ggtgtggctg caggtgacag gaggagagag gttcaatggc ttgtttgctg     720
atgaggacga tgacacaact ttcacagggt tccttctgtt cagcagcccg               770
```

<210> SEQ ID NO 6
<211> LENGTH: 256
<212> TYPE: PRT
<213> ORGANISM: Homo sapiens

<400> SEQUENCE: 6

```
Ala Asp Gly Lys Val Glu Ala Lys Gly Ile Lys Gly Asp Gln Gly Ser
1               5                   10                  15

Arg Gly Ser Pro Gly Lys His Gly Pro Lys Gly Leu Ala Gly Pro Met
            20                  25                  30

Gly Glu Lys Gly Leu Arg Gly Glu Thr Gly Pro Gln Gly Gln Lys Gly
        35                  40                  45

Asn Lys Gly Asp Val Gly Pro Thr Gly Pro Glu Gly Pro Arg Gly Asn
    50                  55                  60

Ile Gly Pro Leu Gly Pro Thr Gly Leu Pro Gly Pro Met Gly Pro Ile
65                  70                  75                  80

Gly Lys Pro Gly Pro Lys Gly Glu Ala Gly Pro Thr Gly Pro Gln Gly
                85                  90                  95

Glu Pro Gly Val Arg Gly Ile Arg Gly Trp Lys Gly Asp Arg Gly Glu
            100                 105                 110

Lys Gly Lys Ile Gly Glu Thr Leu Val Leu Pro Lys Ser Ala Phe Thr
        115                 120                 125

Val Gly Leu Thr Val Leu Ser Lys Phe Pro Ser Ser Asp Met Pro Ile
    130                 135                 140

Lys Phe Asp Lys Ile Leu Tyr Asn Glu Phe Asn His Tyr Asp Thr Ala
145                 150                 155                 160

Ala Gly Lys Phe Thr Cys His Ile Ala Gly Val Tyr Tyr Phe Thr Tyr
                165                 170                 175

His Ile Thr Val Phe Ser Arg Asn Val Gln Val Ser Leu Val Lys Asn
            180                 185                 190

Gly Val Lys Ile Leu His Thr Lys Asp Ala Tyr Met Ser Ser Glu Asp
        195                 200                 205

Gln Ala Ser Gly Gly Ile Val Leu Gln Leu Lys Leu Gly Asp Glu Val
    210                 215                 220

Trp Leu Gln Val Thr Gly Gly Glu Arg Phe Asn Gly Leu Phe Ala Asp
225                 230                 235                 240
```

Glu Asp Asp Asp Thr Thr Phe Thr Gly Phe Leu Leu Phe Ser Ser Pro
            245                 250                 255

<210> SEQ ID NO 7
<211> LENGTH: 999
<212> TYPE: DNA
<213> ORGANISM: Homo sapiens

<400> SEQUENCE: 7
atgaggatct ggtggcttct gcttgccatt gaaatctgca cagggaacat aaactcacag    60
gacacctgca ggcaagggca ccctggaatc cctgggaacc ccggtcacaa tggtctgcct   120
ggaagagatg gacgagacgg agcgaagggt gacaaaggcg atgcaggaga accaggacgt   180
cctggcagcc cggggaagga tgggacgagt ggagagaagg gagaacgagg agcagatgga   240
aaagttgaag caaaaggcat caaaggtgat caaggctcaa gaggatcccc aggaaaacat   300
ggccccaagg ggcttgcagg gcccatggga gagaagggcc tccgaggaga gactgggcct   360
caggggcaga aggggaataa gggtgacgtg gtcccactg gtcctgaggg gccaaggggc   420
aacattgggc ctttgggccc aactggttta ccgggcccca tgggccctat ggaaagcct   480 ggtcccaaag gagaagctgg acccacgggg ccccagggtg agccaggagt ccggggaata   540
agaggctgga aggagatcg aggagagaaa ggaaaatcg gtgagactct agtcttgcca   600
aaaagtgctt tcactgtggg gctcacggtg ctgagcaagt ttccttcttc agatatgccc   660
attaaatttg ataagatcct gtataacgaa ttcaaccatt atgatacagc agcggggaaa   720
ttcacgtgcc acattgctgg ggtctattac ttcacctacc acatcactgt tttctccaga   780
aatgttcagg tgtctttggt caaaaatgga gtaaaaatac tgcacaccaa agatgcttac   840
atgagctctg aggaccaggc ctctggcggc attgtcctgc agctgaagct cggggatgag   900
gtgtggctgc aggtgacagg aggagagagg ttcaatggct tgtttgctga tgaggacgat   960
gacacaactt tcacagggtt ccttctgttc agcagcccg                          999

<210> SEQ ID NO 8
<211> LENGTH: 333
<212> TYPE: PRT
<213> ORGANISM: Homo sapiens

<400> SEQUENCE: 8

Met Arg Ile Trp Trp Leu Leu Leu Ala Ile Glu Ile Cys Thr Gly Asn
1               5                   10                  15

Ile Asn Ser Gln Asp Thr Cys Arg Gln Gly His Pro Gly Ile Pro Gly
            20                  25                  30

Asn Pro Gly His Asn Gly Leu Pro Gly Arg Asp Gly Arg Asp Gly Ala
        35                  40                  45

Lys Gly Asp Lys Gly Asp Ala Gly Glu Pro Gly Arg Pro Gly Ser Pro
    50                  55                  60

Gly Lys Asp Gly Thr Ser Gly Glu Lys Gly Glu Arg Gly Ala Asp Gly
65                  70                  75                  80

Lys Val Glu Ala Lys Gly Ile Lys Gly Asp Gln Gly Ser Arg Gly Ser
                85                  90                  95

Pro Gly Lys His Gly Pro Lys Gly Leu Ala Gly Pro Met Gly Glu Lys
            100                 105                 110

Gly Leu Arg Gly Glu Thr Gly Pro Gln Gly Gln Lys Gly Asn Lys Gly
        115                 120                 125

Asp Val Gly Pro Thr Gly Pro Glu Gly Pro Arg Gly Asn Ile Gly Pro

-continued

```
            130                 135                 140
Leu Gly Pro Thr Gly Leu Pro Gly Pro Met Gly Pro Ile Gly Lys Pro
145                 150                 155                 160

Gly Pro Lys Gly Glu Ala Gly Pro Thr Gly Pro Gln Gly Glu Pro Gly
                165                 170                 175

Val Arg Gly Ile Arg Gly Trp Lys Gly Asp Arg Gly Glu Lys Gly Lys
            180                 185                 190

Ile Gly Glu Thr Leu Val Leu Pro Lys Ser Ala Phe Thr Val Gly Leu
            195                 200                 205

Thr Val Leu Ser Lys Phe Pro Ser Ser Asp Met Pro Ile Lys Phe Asp
210                 215                 220

Lys Ile Leu Tyr Asn Glu Phe Asn His Tyr Asp Thr Ala Ala Gly Lys
225                 230                 235                 240

Phe Thr Cys His Ile Ala Gly Val Tyr Tyr Phe Thr Tyr His Ile Thr
                245                 250                 255

Val Phe Ser Arg Asn Val Gln Val Ser Leu Val Lys Asn Gly Val Lys
                260                 265                 270

Ile Leu His Thr Lys Asp Ala Tyr Met Ser Ser Glu Asp Gln Ala Ser
            275                 280                 285

Gly Gly Ile Val Leu Gln Leu Lys Leu Gly Asp Glu Val Trp Leu Gln
            290                 295                 300

Val Thr Gly Gly Glu Arg Phe Asn Gly Leu Phe Ala Asp Glu Asp Asp
305                 310                 315                 320

Asp Thr Thr Phe Thr Gly Phe Leu Leu Phe Ser Ser Pro
                325                 330

<210> SEQ ID NO 9
<211> LENGTH: 300
<212> TYPE: DNA
<213> ORGANISM: Homo sapiens

<400> SEQUENCE: 9
atgaggatct ggtggcttct gcttgccatt gaaatctgca cagggaacat aaactcacag      60
gacacctgca ggcaagggca ccctggaatc cctgggaacc ccggtcacaa tggtctgcct     120
ggaagagatg gacgagacgg agcgaagggt gacaaaggcg atgcaggaga accaggatgt     180
cctggcagcc cggggaagga tggacgagt ggagagaagg gagaacgagg agcagatgga      240
aaagttgaag caaaaggcat caaaggaatg ttcaggtgtc tttggtcaaa acggagtaa      300

<210> SEQ ID NO 10
<211> LENGTH: 99
<212> TYPE: PRT
<213> ORGANISM: Homo sapiens

<400> SEQUENCE: 10

Met Arg Ile Trp Trp Leu Leu Leu Ala Ile Glu Ile Cys Thr Gly Asn
1               5                   10                  15

Ile Asn Ser Gln Asp Thr Cys Arg Gln Gly His Pro Gly Ile Pro Gly
            20                  25                  30

Asn Pro Gly His Asn Gly Leu Pro Gly Arg Asp Gly Arg Asp Gly Ala
        35                  40                  45

Lys Gly Asp Lys Gly Asp Ala Gly Glu Pro Gly Cys Pro Gly Ser Pro
    50                  55                  60

Gly Lys Asp Gly Thr Ser Gly Glu Lys Gly Glu Arg Gly Ala Asp Gly
65                  70                  75                  80
```

Lys Val Glu Ala Lys Gly Ile Lys Gly Met Phe Arg Cys Leu Trp Ser
            85                  90                  95

Lys Thr Glu

<210> SEQ ID NO 11
<211> LENGTH: 121
<212> TYPE: DNA
<213> ORGANISM: Homo sapiens

<400> SEQUENCE: 11

```
aacataaact cacaggacac ctgcaggcaa gggcaccctg gaatccctgg gaaccccggt    60
cacaatggtc tgcctggaag agatggacga acggagcga agggtgacaa aggcgatgca   120
g                                                                   121
```

<210> SEQ ID NO 12
<211> LENGTH: 41
<212> TYPE: PRT
<213> ORGANISM: Homo sapiens

<400> SEQUENCE: 12

Asn Ile Asn Ser Gln Asp Thr Cys Arg Gln Gly His Pro Gly Ile Pro
1               5                   10                  15

Gly Asn Pro Gly His Asn Gly Leu Pro Gly Arg Asp Gly Arg Asp Gly
            20                  25                  30

Ala Lys Gly Asp Lys Gly Asp Ala Gly
        35                  40

<210> SEQ ID NO 13
<211> LENGTH: 954
<212> TYPE: DNA
<213> ORGANISM: Homo sapiens

<400> SEQUENCE: 13

```
aacataaact cacaggacac ctgcaggcaa gggcaccctg gaatccctgg gaaccccggt    60
cacaatggtc tgcctggaag agatggacga acggagcga agggtgacaa aggcgatgca   120
ggagaaccag gacgtcctgg cagcccgggg aaggatggga cgagtggaga aaggggagaa   180
cgaggagcag atggaaaagt tgaagcaaaa ggcatcaaag gtgatcaagg ctcaagagga   240
tccccaggaa aacatggccc caaggggctt gcagggccca tgggagagaa gggcctccga   300
ggagagactg gcctcaggg gcagaagggg aataagggtg acgtgggtcc cactggtcct   360
gaggggccaa gggcaacat tgggccttg ggcccaactg gtttaccggg ccccatgggc   420
cctattggaa agcctggtcc caaaggagaa gctggaccca cggggcccca gggtgagcca   480
ggagtccggg gaataagagg ctggaaagga gatcgaggag agaaagggaa aatcggtgag   540
actctagtct tgccaaaaag tgctttcact gtggggctca cggtgctgag caagtttcct   600
tcttcagata tgcccattaa atttgataag atcctgtata cgaattcaa ccattatgat   660
acagcagcgg ggaaattcac gtgccacatt gctgggtct attacttcac ctaccacatc   720
actgtttct ccagaaatgt tcaggtgtct ttggtcaaaa atggagtaaa atactgcac   780
accaaagatg cttacatgag ctctgaggac caggcctctg gcggcattgt cctgcagctg   840
aagctcgggg atgaggtgtg gctgcaggtg acaggaggag agaggttcaa tggcttgttt   900
gctgatgagg acgatgacac aactttcaca gggttccttc tgttcagcag cccg         954
```

<210> SEQ ID NO 14
<211> LENGTH: 318

```
<212> TYPE: PRT
<213> ORGANISM: Homo sapiens

<400> SEQUENCE: 14

Asn Ile Asn Ser Gln Asp Thr Cys Arg Gln Gly His Pro Gly Ile Pro
1               5                   10                  15

Gly Asn Pro Gly His Asn Gly Leu Pro Gly Arg Asp Gly Arg Asp Gly
            20                  25                  30

Ala Lys Gly Asp Lys Gly Asp Ala Gly Glu Pro Gly Arg Pro Gly Ser
        35                  40                  45

Pro Gly Lys Asp Gly Thr Ser Gly Glu Lys Gly Glu Arg Gly Ala Asp
50                  55                  60

Gly Lys Val Glu Ala Lys Gly Ile Lys Gly Asp Gln Gly Ser Arg Gly
65                  70                  75                  80

Ser Pro Gly Lys His Gly Pro Lys Gly Leu Ala Gly Pro Met Gly Glu
                85                  90                  95

Lys Gly Leu Arg Gly Glu Thr Gly Pro Gln Gly Gln Lys Gly Asn Lys
            100                 105                 110

Gly Asp Val Gly Pro Thr Gly Pro Glu Gly Pro Arg Gly Asn Ile Gly
        115                 120                 125

Pro Leu Gly Pro Thr Gly Leu Pro Gly Pro Met Gly Pro Ile Gly Lys
130                 135                 140

Pro Gly Pro Lys Gly Glu Ala Gly Pro Thr Gly Pro Gln Gly Glu Pro
145                 150                 155                 160

Gly Val Arg Gly Ile Arg Gly Trp Lys Gly Asp Arg Gly Glu Lys Gly
                165                 170                 175

Lys Ile Gly Glu Thr Leu Val Leu Pro Lys Ser Ala Phe Thr Val Gly
            180                 185                 190

Leu Thr Val Leu Ser Lys Phe Pro Ser Ser Asp Met Pro Ile Lys Phe
        195                 200                 205

Asp Lys Ile Leu Tyr Asn Glu Phe Asn His Tyr Asp Thr Ala Ala Gly
210                 215                 220

Lys Phe Thr Cys His Ile Ala Gly Val Tyr Tyr Phe Thr Tyr His Ile
225                 230                 235                 240

Thr Val Phe Ser Arg Asn Val Gln Val Ser Leu Val Lys Asn Gly Val
                245                 250                 255

Lys Ile Leu His Thr Lys Asp Ala Tyr Met Ser Ser Glu Asp Gln Ala
            260                 265                 270

Ser Gly Gly Ile Val Leu Gln Leu Lys Leu Gly Asp Glu Val Trp Leu
        275                 280                 285

Gln Val Thr Gly Gly Glu Arg Phe Asn Gly Leu Phe Ala Asp Glu Asp
290                 295                 300

Asp Asp Thr Thr Phe Thr Gly Phe Leu Leu Phe Ser Ser Pro
305                 310                 315

<210> SEQ ID NO 15
<211> LENGTH: 255
<212> TYPE: DNA
<213> ORGANISM: Homo sapiens

<400> SEQUENCE: 15
aacataaact cacaggacac ctgcaggcaa gggcaccctg gaatccctgg gaaccccggt      60
cacaatggtc tgcctggaag agatggacga gacggagcga aggtgacaa aggcgatgca     120 ggagaaccag gatgtcctgg cagcccgggg aaggatggga cgagtggaga aagggagaa     180
```

```
cgaggagcag atggaaaagt tgaagcaaaa ggcatcaaag gaatgttcag gtgtctttgg    240
tcaaaaacgg agtaa                                                    255
```

<210> SEQ ID NO 16
<211> LENGTH: 84
<212> TYPE: PRT
<213> ORGANISM: Homo sapiens

<400> SEQUENCE: 16

```
Asn Ile Asn Ser Gln Asp Thr Cys Arg Gln Gly His Pro Gly Ile Pro
1               5                   10                  15

Gly Asn Pro Gly His Asn Gly Leu Pro Gly Arg Asp Gly Arg Asp Gly
            20                  25                  30

Ala Lys Gly Asp Lys Gly Asp Ala Gly Glu Pro Gly Cys Pro Gly Ser
        35                  40                  45

Pro Gly Lys Asp Gly Thr Ser Gly Glu Lys Gly Glu Arg Gly Ala Asp
    50                  55                  60

Gly Lys Val Glu Ala Lys Gly Ile Lys Gly Met Phe Arg Cys Leu Trp
65                  70                  75                  80

Ser Lys Thr Glu
```

<210> SEQ ID NO 17
<211> LENGTH: 22
<212> TYPE: DNA
<213> ORGANISM: Artificial Sequence
<220> FEATURE:
<223> OTHER INFORMATION: INSP058-CP1 primer

<400> SEQUENCE: 17

```
ctggtggctt ctgcttgcca tt                                             22
```

<210> SEQ ID NO 18
<211> LENGTH: 22
<212> TYPE: DNA
<213> ORGANISM: Artificial Sequence
<220> FEATURE:
<223> OTHER INFORMATION: INSP058-CP2 primer

<400> SEQUENCE: 18

```
ggggctgctg aacagaagga ac                                             22
```

<210> SEQ ID NO 19
<211> LENGTH: 37
<212> TYPE: DNA
<213> ORGANISM: Artificial Sequence
<220> FEATURE:
<223> OTHER INFORMATION: GCP forward primer

<400> SEQUENCE: 19

```
ggggacaagt ttgtacaaaa aagcaggctt cgccacc                             37
```

<210> SEQ ID NO 20
<211> LENGTH: 51
<212> TYPE: DNA
<213> ORGANISM: Artificial Sequence
<220> FEATURE:
<223> OTHER INFORMATION: GCP reverse primer

<400> SEQUENCE: 20

```
ggggaccact ttgtacaaga aagctgggtt tcaatggtga tggtgatggt g             51
```

<210> SEQ ID NO 21

```
<211> LENGTH: 45
<212> TYPE: DNA
<213> ORGANISM: Artificial Sequence
<220> FEATURE:
<223> OTHER INFORMATION: INSP058SV-EX1 primer

<400> SEQUENCE: 21
gcaggcttcg ccaccatgag gatctggtgg cttctgcttg ccatt                45

<210> SEQ ID NO 22
<211> LENGTH: 44
<212> TYPE: DNA
<213> ORGANISM: Artificial Sequence
<220> FEATURE:
<223> OTHER INFORMATION: INSP058SV-EX2

<400> SEQUENCE: 22
gtgatggtga tggtgctccg tttttgacca aagacacctg aaca                 44

<210> SEQ ID NO 23
<211> LENGTH: 20
<212> TYPE: DNA
<213> ORGANISM: Artificial Sequence
<220> FEATURE:
<223> OTHER INFORMATION: pEAK12-F primer

<400> SEQUENCE: 23
gccagcttgg cacttgatgt                                            20

<210> SEQ ID NO 24
<211> LENGTH: 20
<212> TYPE: DNA
<213> ORGANISM: Artificial Sequence
<220> FEATURE:
<223> OTHER INFORMATION: pEAK12-R primer

<400> SEQUENCE: 24
gatggaggtg gacgtgtcag                                            20

<210> SEQ ID NO 25
<211> LENGTH: 18
<212> TYPE: DNA
<213> ORGANISM: Artificial Sequence
<220> FEATURE:
<223> OTHER INFORMATION: SP6 primer

<400> SEQUENCE: 25
atttaggtga cactatag                                              18

<210> SEQ ID NO 26
<211> LENGTH: 20
<212> TYPE: DNA
<213> ORGANISM: Artificial Sequence
<220> FEATURE:
<223> OTHER INFORMATION: T7 primer

<400> SEQUENCE: 26
taatacgact cactataggg                                            20
```